(12) United States Patent
Coleman et al.

(10) Patent No.: US 7,618,799 B2
(45) Date of Patent: Nov. 17, 2009

(54) BACTERIAL LEADER SEQUENCES FOR INCREASED EXPRESSION

(75) Inventors: Russell J. Coleman, San Diego, CA (US); Diane Retallack, Poway, CA (US); Jane C. Schneider, San Diego, CA (US); Thomas M. Ramseier, Newton, MA (US); Charles D. Hershberger, Poway, CA (US); Stacey Lee, San Diego, CA (US); Sol M. Resnick, Encinitas, CA (US)

(73) Assignee: Dow Global Technologies Inc, Midland, MI (US)

( * ) Notice: Subject to any disclaimer, the term of this patent is extended or adjusted under 35 U.S.C. 154(b) by 0 days.

(21) Appl. No.: 12/022,789

(22) Filed: Jan. 30, 2008

(65) Prior Publication Data

US 2008/0193974 A1 Aug. 14, 2008

Related U.S. Application Data

(60) Provisional application No. 60/887,476, filed on Jan. 31, 2007, provisional application No. 60/887,486, filed on Jan. 31, 2007.

(51) Int. Cl.
C12N 9/00 (2006.01)
C12N 15/00 (2006.01)
C12N 1/04 (2006.01)

(52) U.S. Cl. ................. 435/183; 435/252.3; 435/320.1; 536/23.1

(58) Field of Classification Search .................. 435/183, 435/252.3, 320.1; 536/23.2
See application file for complete search history.

(56) References Cited

U.S. PATENT DOCUMENTS 5,629,172 A * 5/1997 Mascarenhas et al. ....... 435/69.7
5,801,017 A * 9/1998 Werber et al. ............... 435/69.2

FOREIGN PATENT DOCUMENTS

WO WO 2005/089093 A2 9/2005

OTHER PUBLICATIONS

Paulson et al., Nature Biotechnology, 23, 873-878, 2005.*

NCBI Report for Accession No. YP_346180, Direct Submission on Aug. 8, 2005.
Huber, D., "Use of Thioredoxin as a Reporter to Identify a Subset of *Escherichia coli* Signal Sequences That Promote Signal Recognition Particle-Dependent Translocation," *Journal of Bacteriology*, 2005, pp. 2983-2991, vol. 187 (9).
Miot, M. and Betton, J., "Protein Quality Control in the Bacterial Periplasm," *Microbial Cell Factories*, 2004, pp. 1-13.
Ma, Q., et al., "Protein Secretion Systems of *Pseudomonas aeruginosa* and *P. fluorescens*," *Biochim. Biophys. Acta*, Apr. 1, 2003, pp. 223-233, vol. 1611, No. 1-2.
Retallack, D.M., et al.,"Transport of Heterologous Proteins to the Periplasmic Space of *Pseudomonas fluorescens* Using a Variety of Native Signal Sequences, " *Biotechnol Lett*, Oct. 2007, pp. 1483-1491, vol. 29, No. 10.
Urban, A., et al., "DsbA and DsbC Affect Extracellular Enzyme Formation in *Pseudomonas aeruginosa*," *J. Bacteriol.*, Jan. 2001, pp. 587-596, vol. 183, No. 2.
Wang, H., et al., "High-level Expression of Human TFF3 in *Escherichia coli*," *Peptides*, Jul. 1, 2005, pp. 1213-1218, vol. 26, No. 7.
EMBL Database Accession No. AF057031, Submitted Apr. 2, 1998 (XP-002483318).
NCBI Database Accession No. Q3KHI7, Direct Submission Aug. 2005 (SP-002483317).

* cited by examiner

*Primary Examiner*—Maryam Monshipouri
(74) *Attorney, Agent, or Firm*—Jarett Abramson; Alston & Bird LLP

(57) ABSTRACT

Compositions and methods for improving expression and/or secretion of protein or polypeptide of interest in a host cell are provided. Compositions comprising a coding sequence for a bacterial secretion signal peptide are provided. The coding sequences can be used in vector constructs or expression systems for transformation and expression of a protein or polypeptide of interest in a host cell. The compositions of the invention are useful for increasing accumulation of properly processed proteins in the periplasmic space of a host cell, or for increasing secretion of properly processed proteins from the host cell. In particular, isolated secretion signal peptide-encoding nucleic acid molecules are provided. Additionally, amino acid sequences corresponding to the nucleic acid molecules are encompassed. In particular, the present invention provides for isolated nucleic acid molecules comprising nucleotide sequences encoding the amino acid sequences shown in SEQ ID NO: 2, 4, 6, 8, 10, 12, 14, 16, 18, 20, 22, and 24, and the nucleotide sequences set forth in SEQ ID NO: 1, 3, 5, 7, 9, 11, 13, 15, 17, 19, 21, and 23, as well as variants and fragments thereof.

68 Claims, 11 Drawing Sheets

SEQUENCE LISTING

```
<160> NUMBER OF SEQ ID NOS: 50

<210> SEQ ID NO 1
<211> LENGTH: 72
<212> TYPE: DNA
<213> ORGANISM: Artificial Sequence
<220> FEATURE:
<223> OTHER INFORMATION: mutant phosphate binding protein leader
      sequence (pbp*)
<221> NAME/KEY: CDS
<222> LOCATION: (1)...(72)

<400> SEQUENCE: 1 atg aaa ctg aaa cgt ttg atg gcg gca atg act ttt gtc gct gct ggc      48
Met Lys Leu Lys Arg Leu Met Ala Ala Met Thr Phe Val Ala Ala Gly
1               5                   10                  15 gtt gcg acc gtc aac gcg gtg gcc                                       72
Val Ala Thr Val Asn Ala Val Ala
            20

<210> SEQ ID NO 2
<211> LENGTH: 24
<212> TYPE: PRT
<213> ORGANISM: Artificial Sequence
<220> FEATURE:
<223> OTHER INFORMATION: mutant phosphate binding protein leader
      sequence (pbp*)

<400> SEQUENCE: 2

Met Lys Leu Lys Arg Leu Met Ala Ala Met Thr Phe Val Ala Ala Gly
1               5                   10                  15

Val Ala Thr Val Asn Ala Val Ala
            20

<210> SEQ ID NO 3
<211> LENGTH: 66
<212> TYPE: DNA
<213> ORGANISM: Pseudomonas fluorescens
<220> FEATURE:
<221> NAME/KEY: CDS
<222> LOCATION: (1)...(66)

<400> SEQUENCE: 3 atg cgt aat ctg atc ctc agc gcc gct ctc gtc act gcc agc ctc ttc      48
Met Arg Asn Leu Ile Leu Ser Ala Ala Leu Val Thr Ala Ser Leu Phe
1               5                   10                  15 ggc atg acc gca caa gct                                               66
Gly Met Thr Ala Gln Ala
            20

<210> SEQ ID NO 4
<211> LENGTH: 22
<212> TYPE: PRT
```

```
<213> ORGANISM: Pseudomonas fluorescens

<400> SEQUENCE: 4

Met Arg Asn Leu Ile Leu Ser Ala Ala Leu Val Thr Ala Ser Leu Phe
1               5                   10                  15

Gly Met Thr Ala Gln Ala
        20

<210> SEQ ID NO 5
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 5 atg cgc ttg acc cag att att gcc gcc gca gcc att gcg ttg gtt tcc    48
Met Arg Leu Thr Gln Ile Ile Ala Ala Ala Ala Ile Ala Leu Val Ser
1               5                   10                  15 acc ttt gcg ctc gcc                                                63
Thr Phe Ala Leu Ala
        20

<210> SEQ ID NO 6
<211> LENGTH: 21
<212> TYPE: PRT
<213> ORGANISM: Pseudomonas fluorescens

<400> SEQUENCE: 6

Met Arg Leu Thr Gln Ile Ile Ala Ala Ala Ala Ile Ala Leu Val Ser
1               5                   10                  15

Thr Phe Ala Leu Ala
        20

<210> SEQ ID NO 7
<211> LENGTH: 99
<212> TYPE: DNA
<213> ORGANISM: Bacillus coagulans
<220> FEATURE:
<221> NAME/KEY: CDS
<222> LOCATION: (1)...(99)

<400> SEQUENCE: 7 atg agc aca cga atc ccc cgc cga caa tgg ctg aaa ggc gcc tcg ggc    48
Met Ser Thr Arg Ile Pro Arg Arg Gln Trp Leu Lys Gly Ala Ser Gly
1               5                   10                  15 ctg ctg gcc gcc gcg agc ctg ggc cgg ttg gcc aac cgc gag gcg cgc    96
Leu Leu Ala Ala Ala Ser Leu Gly Arg Leu Ala Asn Arg Glu Ala Arg
        20                  25                  30 gcc                                                                99
Ala

<210> SEQ ID NO 8
<211> LENGTH: 33
<212> TYPE: PRT
<213> ORGANISM: Bacillus coagulans

<400> SEQUENCE: 8

Met Ser Thr Arg Ile Pro Arg Arg Gln Trp Leu Lys Gly Ala Ser Gly
1               5                   10                  15

Leu Leu Ala Ala Ala Ser Leu Gly Arg Leu Ala Asn Arg Glu Ala Arg
        20                  25                  30
```

Ala

<210> SEQ ID NO 9
<211> LENGTH: 75
<212> TYPE: DNA
<213> ORGANISM: Pseudomonas fluorescens
<220> FEATURE:
<221> NAME/KEY: CDS
<222> LOCATION: (1)...(75)

<400> SEQUENCE: 9

```
atg tcg tgc aca cgt gca ttc aaa cca ctg ctg ctg atc ggc ctg gcc      48
Met Ser Cys Thr Arg Ala Phe Lys Pro Leu Leu Leu Ile Gly Leu Ala
1               5                   10                  15 aca ctg atg tgt tcc cat gca ttc gct                                  75
Thr Leu Met Cys Ser His Ala Phe Ala
            20                  25
```

<210> SEQ ID NO 10
<211> LENGTH: 25
<212> TYPE: PRT
<213> ORGANISM: Pseudomonas fluorescens

<400> SEQUENCE: 10

```
Met Ser Cys Thr Arg Ala Phe Lys Pro Leu Leu Leu Ile Gly Leu Ala
1               5                   10                  15

Thr Leu Met Cys Ser His Ala Phe Ala
            20                  25
```

<210> SEQ ID NO 11
<211> LENGTH: 72
<212> TYPE: DNA
<213> ORGANISM: Pseudomonas fluorescens
<220> FEATURE:
<221> NAME/KEY: CDS
<222> LOCATION: (1)...(72)

<400> SEQUENCE: 11

```
atg ctt ttt cgc aca tta ctg gcg agc ctt acc ttt gct gtc atc gcc      48
Met Leu Phe Arg Thr Leu Leu Ala Ser Leu Thr Phe Ala Val Ile Ala
1               5                   10                  15 ggc tta ccg tcc acg gcc cac gcg                                      72
Gly Leu Pro Ser Thr Ala His Ala
            20
```

<210> SEQ ID NO 12
<211> LENGTH: 24
<212> TYPE: PRT
<213> ORGANISM: Pseudomonas fluorescens

<400> SEQUENCE: 12

```
Met Leu Phe Arg Thr Leu Leu Ala Ser Leu Thr Phe Ala Val Ile Ala
1               5                   10                  15

Gly Leu Pro Ser Thr Ala His Ala
            20
```

<210> SEQ ID NO 13
<211> LENGTH: 69
<212> TYPE: DNA
<213> ORGANISM: Pseudomonas fluorescens
<220> FEATURE:
<221> NAME/KEY: CDS
<222> LOCATION: (1)...(69)

<400> SEQUENCE: 13

```
atg ccg cct cgt tct atc gcc gca tgt ctg ggg ctg ctg ggc ttg ctc      48
Met Pro Pro Arg Ser Ile Ala Ala Cys Leu Gly Leu Leu Gly Leu Leu
1               5                   10                  15 atg gct acc cag gcc gcc gcc                                           69
Met Ala Thr Gln Ala Ala Ala
            20

<210> SEQ ID NO 14
<211> LENGTH: 23
<212> TYPE: PRT
<213> ORGANISM: Pseudomonas fluorescens

<400> SEQUENCE: 14

Met Pro Pro Arg Ser Ile Ala Ala Cys Leu Gly Leu Leu Gly Leu Leu
1               5                   10                  15

Met Ala Thr Gln Ala Ala Ala
            20

<210> SEQ ID NO 15
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 15 atg cgc ctc gct gcc cta ccg cta ttg ctt gcc cct ctc ttt att gcg      48
Met Arg Leu Ala Ala Leu Pro Leu Leu Leu Ala Pro Leu Phe Ile Ala
1               5                   10                  15 ccg atg gcc gtt gcg                                                   63
Pro Met Ala Val Ala
            20

<210> SEQ ID NO 16
<211> LENGTH: 21
<212> TYPE: PRT
<213> ORGANISM: Pseudomonas fluorescens

<400> SEQUENCE: 16

Met Arg Leu Ala Ala Leu Pro Leu Leu Leu Ala Pro Leu Phe Ile Ala
1               5                   10                  15

Pro Met Ala Val Ala
            20

<210> SEQ ID NO 17
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 17 atg aag ttc aaa cag ctg atg gcg atg gcg ctt ttg ttg gcc ttg agc      48
Met Lys Phe Lys Gln Leu Met Ala Met Ala Leu Leu Leu Ala Leu Ser
1               5                   10                  15 gct gtg gcc cag gcc                                                   63
Ala Val Ala Gln Ala
            20

<210> SEQ ID NO 18
<211> LENGTH: 21
<212> TYPE: PRT
<213> ORGANISM: Pseudomonas fluorescens
```

<400> SEQUENCE: 18

Met Lys Phe Lys Gln Leu Met Ala Met Ala Leu Leu Leu Ala Leu Ser
1               5                   10                  15

Ala Val Ala Gln Ala
            20

<210> SEQ ID NO 19
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 19 atg aat aga tct tcc gcg ttg ctc ctc gct ttt gtc ttc ctc agc ggc    48
Met Asn Arg Ser Ser Ala Leu Leu Leu Ala Phe Val Phe Leu Ser Gly
1               5                   10                  15 tgc cag gcc atg gcc                                                63
Cys Gln Ala Met Ala
            20

<210> SEQ ID NO 20
<211> LENGTH: 21
<212> TYPE: PRT
<213> ORGANISM: Pseudomonas fluorescens

<400> SEQUENCE: 20

Met Asn Arg Ser Ser Ala Leu Leu Leu Ala Phe Val Phe Leu Ser Gly
1               5                   10                  15

Cys Gln Ala Met Ala
            20

<210> SEQ ID NO 21
<211> LENGTH: 99
<212> TYPE: DNA
<213> ORGANISM: Pseudomonas fluorescens
<220> FEATURE:
<221> NAME/KEY: CDS
<222> LOCATION: (1)...(99)

<400> SEQUENCE: 21 atg caa aac cgc act gtg gaa atc ggt gtc ggc ctt ttc ttg ctg gct    48
Met Gln Asn Arg Thr Val Glu Ile Gly Val Gly Leu Phe Leu Leu Ala
1               5                   10                  15 ggc atc ctg gct tta ctg ttg ttg gcc ctg cga gtc agc ggc ctt tcg    96
Gly Ile Leu Ala Leu Leu Leu Leu Ala Leu Arg Val Ser Gly Leu Ser
            20                  25                  30 gcc                                                                99
Ala

<210> SEQ ID NO 22
<211> LENGTH: 33
<212> TYPE: PRT
<213> ORGANISM: Pseudomonas fluorescens

<400> SEQUENCE: 22

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala

<210> SEQ ID NO 23
<211> LENGTH: 117
<212> TYPE: DNA
<213> ORGANISM: Pseudomonas fluorescens
<220> FEATURE:
<221> NAME/KEY: CDS
<222> LOCATION: (1)...(117)

<400> SEQUENCE: 23

```
atg tct ctt cgt aat atg aat atc gcc ccg agg gcc ttc ctc ggc ttc        48
Met Ser Leu Arg Asn Met Asn Ile Ala Pro Arg Ala Phe Leu Gly Phe
1               5                   10                  15 gcg ttt att ggc gcc ttg atg ttg ttg ctc ggt gtg ttc gcg ctg aac        96
Ala Phe Ile Gly Ala Leu Met Leu Leu Leu Gly Val Phe Ala Leu Asn
20                  25                  30 cag atg agc aaa att cgt gcg                                            117
Gln Met Ser Lys Ile Arg Ala
35
```

<210> SEQ ID NO 24
<211> LENGTH: 39
<212> TYPE: PRT
<213> ORGANISM: Pseudomonas fluorescens

<400> SEQUENCE: 24

Met Ser Leu Arg Asn Met Asn Ile Ala Pro Arg Ala Phe Leu Gly Phe
1               5                   10                  15

Ala Phe Ile Gly Ala Leu Met Leu Leu Leu Gly Val Phe Ala Leu Asn
20                  25                  30

Gln Met Ser Lys Ile Arg Ala
35

<210> SEQ ID NO 25
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 25
aattactagt aggaggtaca ttatgcgctt                                       30

<210> SEQ ID NO 26
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 26
tatactcgag ttatttaacc tgtttcagta                                       30

<210> SEQ ID NO 27
<211> LENGTH: 5
<212> TYPE: PRT
<213> ORGANISM: Artificial Sequence
<220> FEATURE:
<223> OTHER INFORMATION: First 5 amino acids of the predicted protein
      sequence for the processed form of dsbC-Skp

<400> SEQUENCE: 27

Ala Asp Lys Ile Ala
1               5

<210> SEQ ID NO 28
<211> LENGTH: 10
<212> TYPE: PRT
<213> ORGANISM: Artificial Sequence
<220> FEATURE:
<223> OTHER INFORMATION: First 10 amino acids of the predicted protein
      sequence for the unprocessed form of dsbC-Skp

<400> SEQUENCE: 28

Met Arg Leu Thr Gln Ile Ile Ala Ala Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: First 10 amino acids of the predicted protein
      sequence for the processed form of dsbC-Skp

<400> SEQUENCE: 29

Ala Asp Lys Ile Ala Ile Val Asn Met Gly
1               5                   10

<210> SEQ ID NO 30
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 30 atg aag aag tcc acc ttg gct gtg gct gta acg ttg ggc gca atc gcc      48
Met Lys Lys Ser Thr Leu Ala Val Ala Val Thr Leu Gly Ala Ile Ala
1               5                   10                  15 cag caa gca ggc gct                                                  63
Gln Gln Ala Gly Ala
            20

<210> SEQ ID NO 31
<211> LENGTH: 21
<212> TYPE: PRT
<213> ORGANISM: Pseudomonas fluorescens

<400> SEQUENCE: 31

Met Lys Lys Ser Thr Leu Ala Val Ala Val Thr Leu Gly Ala Ile Ala
1               5                   10                  15

Gln Gln Ala Gly Ala
            20

<210> SEQ ID NO 32
<211> LENGTH: 72
<212> TYPE: DNA
<213> ORGANISM: Pseudomonas fluorescens
<220> FEATURE:
<221> NAME/KEY: CDS
<222> LOCATION: (1)...(72)

<400> SEQUENCE: 32 atg aaa ctg aaa aac acc ttg ggc ttg gcc att ggt tct ctt att gcc      48
Met Lys Leu Lys Asn Thr Leu Gly Leu Ala Ile Gly Ser Leu Ile Ala
1               5                   10                  15 gct act tct ttc ggc gtt ctg gca                                      72
Ala Thr Ser Phe Gly Val Leu Ala
            20

```
<210> SEQ ID NO 33
<211> LENGTH: 24
<212> TYPE: PRT
<213> ORGANISM: Pseudomonas fluorescens

<400> SEQUENCE: 33

Met Lys Leu Lys Asn Thr Leu Gly Leu Ala Ile Gly Ser Leu Ile Ala
1               5                   10                  15

Ala Thr Ser Phe Gly Val Leu Ala
        20

<210> SEQ ID NO 34
<211> LENGTH: 72
<212> TYPE: DNA
<213> ORGANISM: Pseudomonas fluorescens
<220> FEATURE:
<221> NAME/KEY: CDS
<222> LOCATION: (1)...(72)

<400> SEQUENCE: 34 atg aaa ctg aaa cgt ttg atg gcg gca atg act ttt gtc gct gct ggc      48
Met Lys Leu Lys Arg Leu Met Ala Ala Met Thr Phe Val Ala Ala Gly
1               5                   10                  15 gtt gcg acc gcc aac gcg gtg gcc                                      72
Val Ala Thr Ala Asn Ala Val Ala
        20

<210> SEQ ID NO 35
<211> LENGTH: 24
<212> TYPE: PRT
<213> ORGANISM: Pseudomonas fluorescens

<400> SEQUENCE: 35

Met Lys Leu Lys Arg Leu Met Ala Ala Met Thr Phe Val Ala Ala Gly
1               5                   10                  15

Val Ala Thr Ala Asn Ala Val Ala
        20

<210> SEQ ID NO 36
<211> LENGTH: 60
<212> TYPE: DNA
<213> ORGANISM: Pseudomonas fluorescens
<220> FEATURE:
<221> NAME/KEY: CDS
<222> LOCATION: (1)...(60)

<400> SEQUENCE: 36 atg ttt gcc aaa ctc gtt gct gtt tcc ctg ctg act ctg gca agc ggc      48
Met Phe Ala Lys Leu Val Ala Val Ser Leu Leu Thr Leu Ala Ser Gly
1               5                   10                  15 cag ttg ctt gct                                                      60
Gln Leu Leu Ala
        20

<210> SEQ ID NO 37
<211> LENGTH: 20
<212> TYPE: PRT
<213> ORGANISM: Pseudomonas fluorescens

<400> SEQUENCE: 37

Met Phe Ala Lys Leu Val Ala Val Ser Leu Leu Thr Leu Ala Ser Gly
1               5                   10                  15

Gln Leu Leu Ala
```

20

```
<210> SEQ ID NO 38
<211> LENGTH: 51
<212> TYPE: DNA
<213> ORGANISM: Pseudomonas fluorescens
<220> FEATURE:
<221> NAME/KEY: CDS
<222> LOCATION: (1)...(51)

<400> SEQUENCE: 38 atg atc aaa cgc aat ctg ctg gtt atg ggc ctt gcc gtg ctg ttg agc      48
Met Ile Lys Arg Asn Leu Leu Val Met Gly Leu Ala Val Leu Leu Ser
1               5                   10                  15 gct                                                                  51
Ala

<210> SEQ ID NO 39
<211> LENGTH: 17
<212> TYPE: PRT
<213> ORGANISM: Pseudomonas fluorescens

<400> SEQUENCE: 39

Met Ile Lys Arg Asn Leu Leu Val Met Gly Leu Ala Val Leu Leu Ser
1               5                   10                  15

Ala

<210> SEQ ID NO 40
<211> LENGTH: 69
<212> TYPE: DNA
<213> ORGANISM: Pseudomonas fluorescens
<220> FEATURE:
<221> NAME/KEY: CDS
<222> LOCATION: (1)...(69)

<400> SEQUENCE: 40 atg cag aac tat aaa aaa ttc ctt ctg gcc gcg gcc gtc tcg atg gcg      48
Met Gln Asn Tyr Lys Lys Phe Leu Leu Ala Ala Ala Val Ser Met Ala
1               5                   10                  15 ttc agc gcc acg gcc atg gca                                          69
Phe Ser Ala Thr Ala Met Ala
20

<210> SEQ ID NO 41
<211> LENGTH: 23
<212> TYPE: PRT
<213> ORGANISM: Pseudomonas fluorescens

<400> SEQUENCE: 41

Met Gln Asn Tyr Lys Lys Phe Leu Leu Ala Ala Ala Val Ser Met Ala
1               5                   10                  15

Phe Ser Ala Thr Ala Met Ala
20

<210> SEQ ID NO 42
<211> LENGTH: 93
<212> TYPE: DNA
<213> ORGANISM: Pseudomonas fluorescens
<220> FEATURE:
<221> NAME/KEY: CDS
<222> LOCATION: (1)...(93)

<400> SEQUENCE: 42 atg atc cgt gac aac cga ctc aag aca tcc ctt ctg cgc ggc ctg acc      48
Met Ile Arg Asp Asn Arg Leu Lys Thr Ser Leu Leu Arg Gly Leu Thr
```

```
                        1               5                  10                 15
ctc acc cta ctc agc ctg acc ctg ctc tcg ccc gcg gcc cat tct         93
Leu Thr Leu Leu Ser Leu Thr Leu Leu Ser Pro Ala Ala His Ser
 20                  25                 30

<210> SEQ ID NO 43
<211> LENGTH: 31
<212> TYPE: PRT
<213> ORGANISM: Pseudomonas fluorescens

<400> SEQUENCE: 43

Met Ile Arg Asp Asn Arg Leu Lys Thr Ser Leu Leu Arg Gly Leu Thr
 1               5                  10                 15

Leu Thr Leu Leu Ser Leu Thr Leu Leu Ser Pro Ala Ala His Ser
 20                  25                 30

<210> SEQ ID NO 44
<211> LENGTH: 5
<212> TYPE: PRT
<213> ORGANISM: Artificial Sequence
<220> FEATURE:
<223> OTHER INFORMATION: N-terminal amino acid sequence of
      processed azurin and ibp

<400> SEQUENCE: 44

Ala Gln Val Gln Leu
 1               5

<210> SEQ ID NO 45
<211> LENGTH: 1317
<212> TYPE: DNA
<213> ORGANISM: Bacillus coagulans
<220> FEATURE:
<221> NAME/KEY: CDS
<222> LOCATION: (1)...(1317)

<400> SEQUENCE: 45 atg agc aca cga atc ccc cgc cga caa tgg ctg aaa ggc gcc tcg ggc         48
Met Ser Thr Arg Ile Pro Arg Arg Gln Trp Leu Lys Gly Ala Ser Gly
 1               5                  10                 15 ctg ctg gcc gcc gcg agc ctg ggc cgg ttg gcc aac cgc gag gcg cgc         96
Leu Leu Ala Ala Ala Ser Leu Gly Arg Leu Ala Asn Arg Glu Ala Arg
 20                  25                 30 gcc gcc gaa gcg agc gcc gcc gcg ccg ctc gac act ggc tcg ctg ggc        144
Ala Ala Glu Ala Ser Ala Ala Ala Pro Leu Asp Thr Gly Ser Leu Gly
 35                  40                 45 gcc tcg ccg cgc gcg acg ctc gac gcc tgc ctg caa aaa gcc gtc gac        192
Ala Ser Pro Arg Ala Thr Leu Asp Ala Cys Leu Gln Lys Ala Val Asp
 50                  55                 60 gac ggc acg ctc aag agc gtg gtg gcg atg gcc gcc acc gag cgc ggg        240
Asp Gly Thr Leu Lys Ser Val Val Ala Met Ala Ala Thr Glu Arg Gly
 65                  70                 75                 80 ctc gcc tac cag ggc gcg cgc ggc ccg gcc aac gcg gcc ggc gag ccg        288
Leu Ala Tyr Gln Gly Ala Arg Gly Pro Ala Asn Ala Ala Gly Glu Pro
 85                  90                 95 atc ggc ccc gat acg gtg ttc tgg atg ctg tcg atg acc aag gcg atc        336
Ile Gly Pro Asp Thr Val Phe Trp Met Leu Ser Met Thr Lys Ala Ile
100                  105                110 acc gcc acc gcc tgc atg cag ctg atc gag cag ggc cgg ctc ggg ctc        384
Thr Ala Thr Ala Cys Met Gln Leu Ile Glu Gln Gly Arg Leu Gly Leu
115                  120                125 gac cag ccc gcc gcc gag atc ctg ccg caa ctg aag gcg ccg cag gtg        432
Asp Gln Pro Ala Ala Glu Ile Leu Pro Gln Leu Lys Ala Pro Gln Val
```

```
         130                 135                 140
ctg gag ggc ttc gac gcc gcc ggc cag ccc agg ctg cgc ccg gcg cgc    480
Leu Glu Gly Phe Asp Ala Ala Gly Gln Pro Arg Leu Arg Pro Ala Arg
145                 150                 155                 160 cgc gcg atc acg gtg cgc cac ctg ctc acg cat acc tcg ggc tat acc    528
Arg Ala Ile Thr Val Arg His Leu Leu Thr His Thr Ser Gly Tyr Thr
165                 170                 175 tac agc atc tgg agc gag gcg ctg ggc cgc tac gaa cag gtc acg ggc    576
Tyr Ser Ile Trp Ser Glu Ala Leu Gly Arg Tyr Glu Gln Val Thr Gly
180                 185                 190 atg ccc gac atc ggc tac tcg ctg aac ggc gcc ttc gcg gcc ccg ctc    624
Met Pro Asp Ile Gly Tyr Ser Leu Asn Gly Ala Phe Ala Ala Pro Leu
195                 200                 205 gaa ttc gag ccc ggc gag cgc tgg caa tac ggc atc ggc atg gat tgg    672
Glu Phe Glu Pro Gly Glu Arg Trp Gln Tyr Gly Ile Gly Met Asp Trp
210                 215                 220 gtg ggc aag ctg gtg gag gcg gtg acc gac cag tcg ctg gaa gtg gcg    720
Val Gly Lys Leu Val Glu Ala Val Thr Asp Gln Ser Leu Glu Val Ala
225                 230                 235                 240 ttc cgc gag cgg atc ttc gcg ccg ctc ggc atg cac gat acg ggc ttc    768
Phe Arg Glu Arg Ile Phe Ala Pro Leu Gly Met His Asp Thr Gly Phe
245                 250                 255 ctg atc ggc agc gcg caa aag cgc cgc gtc gcc acg ctg cat cgg cgc    816
Leu Ile Gly Ser Ala Gln Lys Arg Arg Val Ala Thr Leu His Arg Arg
260                 265                 270 cag gcc gat ggc tcg ctg acg ccg gaa ccc ttc gag acc aac cag cgg    864
Gln Ala Asp Gly Ser Leu Thr Pro Glu Pro Phe Glu Thr Asn Gln Arg
275                 280                 285 ccc gag ttc ttc atg ggc ggc ggc ggg ctg ttc agc acc ccg cgc gac    912
Pro Glu Phe Phe Met Gly Gly Gly Gly Leu Phe Ser Thr Pro Arg Asp
290                 295                 300 tac ctc gcc ttc ctg cag atg ctg ctg aac ggc ggc gcc tgg cgc ggc    960
Tyr Leu Ala Phe Leu Gln Met Leu Leu Asn Gly Gly Ala Trp Arg Gly
305                 310                 315                 320 gag cgg ctg ctg cgg ccc gac acc gtg gcg agc atg ttc cgc aac cag   1008
Glu Arg Leu Leu Arg Pro Asp Thr Val Ala Ser Met Phe Arg Asn Gln
325                 330                 335 atc ggc gat ctt cag gtt cgc gaa atg aag acc gcc cag ccg gcc tgg   1056
Ile Gly Asp Leu Gln Val Arg Glu Met Lys Thr Ala Gln Pro Ala Trp
340                 345                 350 tcg aac agc ttc gac caa ttc ccc ggc gcg acg cac aag tgg ggg ctg   1104
Ser Asn Ser Phe Asp Gln Phe Pro Gly Ala Thr His Lys Trp Gly Leu
355                 360                 365 tcc ttc gat ctc aac agc gag ccg ggg ccg cac ggg cgc ggc gcc ggc   1152
Ser Phe Asp Leu Asn Ser Glu Pro Gly Pro His Gly Arg Gly Ala Gly
370                 375                 380 tcg ggt agc tgg gcc ggc ctg ctg aac acc tac ttc tgg atc gat ccc   1200
Ser Gly Ser Trp Ala Gly Leu Leu Asn Thr Tyr Phe Trp Ile Asp Pro
385                 390                 395                 400 gcc aag cgc gtg acg ggg gcg ctg ttc acg cag atg ctg ccg ttc tac   1248
Ala Lys Arg Val Thr Gly Ala Leu Phe Thr Gln Met Leu Pro Phe Tyr
405                 410                 415 gac gcg cgc gtg gtc gat ctc tac ggg cgc ttc gag cgc ggg ctc tac   1296
Asp Ala Arg Val Val Asp Leu Tyr Gly Arg Phe Glu Arg Gly Leu Tyr
420                 425                 430 gac ggg ctg ggc cgc gcc tga                                       1317
Asp Gly Leu Gly Arg Ala  *
435
```

<210> SEQ ID NO 46
<211> LENGTH: 438
<212> TYPE: PRT
<213> ORGANISM: Bacillus coagulans

<400> SEQUENCE: 46

```
Met Ser Thr Arg Ile Pro Arg Arg Gln Trp Leu Lys Gly Ala Ser Gly
1               5                   10                  15

Leu Leu Ala Ala Ser Leu Gly Arg Leu Ala Asn Arg Glu Ala Arg
        20                  25                  30

Ala Ala Glu Ala Ser Ala Ala Pro Leu Asp Thr Gly Ser Leu Gly
    35                  40                  45

Ala Ser Pro Arg Ala Thr Leu Asp Ala Cys Leu Gln Lys Ala Val Asp
50                  55                  60

Asp Gly Thr Leu Lys Ser Val Val Ala Met Ala Thr Glu Arg Gly
65                  70                  75                  80

Leu Ala Tyr Gln Gly Ala Arg Gly Pro Ala Asn Ala Ala Gly Glu Pro
        85                  90                  95

Ile Gly Pro Asp Thr Val Phe Trp Met Leu Ser Met Thr Lys Ala Ile
100                 105                 110

Thr Ala Thr Ala Cys Met Gln Leu Ile Glu Gln Gly Arg Leu Gly Leu
115                 120                 125

Asp Gln Pro Ala Ala Glu Ile Leu Pro Gln Leu Lys Ala Pro Gln Val
130                 135                 140

Leu Glu Gly Phe Asp Ala Ala Gly Gln Pro Arg Leu Arg Pro Ala Arg
145                 150                 155                 160

Arg Ala Ile Thr Val Arg His Leu Leu Thr His Thr Ser Gly Tyr Thr
            165                 170                 175

Tyr Ser Ile Trp Ser Glu Ala Leu Gly Arg Tyr Glu Gln Val Thr Gly
        180                 185                 190

Met Pro Asp Ile Gly Tyr Ser Leu Asn Gly Ala Phe Ala Ala Pro Leu
    195                 200                 205

Glu Phe Glu Pro Gly Glu Arg Trp Gln Tyr Gly Ile Gly Met Asp Trp
210                 215                 220

Val Gly Lys Leu Val Glu Ala Val Thr Asp Gln Ser Leu Glu Val Ala
225                 230                 235                 240

Phe Arg Glu Arg Ile Phe Ala Pro Leu Gly Met His Asp Thr Gly Phe
            245                 250                 255

Leu Ile Gly Ser Ala Gln Lys Arg Arg Val Ala Thr Leu His Arg Arg
        260                 265                 270

Gln Ala Asp Gly Ser Leu Thr Pro Glu Pro Phe Glu Thr Asn Gln Arg
    275                 280                 285

Pro Glu Phe Phe Met Gly Gly Gly Leu Phe Ser Thr Pro Arg Asp
290                 295                 300

Tyr Leu Ala Phe Leu Gln Met Leu Leu Asn Gly Gly Ala Trp Arg Gly
305                 310                 315                 320

Glu Arg Leu Leu Arg Pro Asp Thr Val Ala Ser Met Phe Arg Asn Gln
            325                 330                 335

Ile Gly Asp Leu Gln Val Arg Glu Met Lys Thr Ala Gln Pro Ala Trp
        340                 345                 350

Ser Asn Ser Phe Asp Gln Phe Pro Gly Ala Thr His Lys Trp Gly Leu
    355                 360                 365

Ser Phe Asp Leu Asn Ser Glu Pro Gly Pro His Gly Arg Gly Ala Gly
370                 375                 380
```

```
Ser Gly Ser Trp Ala Gly Leu Leu Asn Thr Tyr Phe Trp Ile Asp Pro
385                 390                 395                 400

Ala Lys Arg Val Thr Gly Ala Leu Phe Thr Gln Met Leu Pro Phe Tyr
            405                 410                 415

Asp Ala Arg Val Val Asp Leu Tyr Gly Arg Phe Glu Arg Gly Leu Tyr
420                 425                 430

Asp Gly Leu Gly Arg Ala
435

<210> SEQ ID NO 47
<211> LENGTH: 324
<212> TYPE: DNA
<213> ORGANISM: Escherichia coli
<220> FEATURE:
<221> NAME/KEY: CDS
<222> LOCATION: (1)...(324)

<400> SEQUENCE: 47 agc gat aaa att att cac ctg act gac gac agt ttt gac acg gat gta      48
Ser Asp Lys Ile Ile His Leu Thr Asp Asp Ser Phe Asp Thr Asp Val
1               5                   10                  15 ctc aaa gcg gac ggg gcg atc ctc gtc gat ttc tgg gca gag tgg tgc      96
Leu Lys Ala Asp Gly Ala Ile Leu Val Asp Phe Trp Ala Glu Trp Cys
            20                  25                  30 ggt ccg tgc aaa atg atc gcc ccg att ctg gat gaa atc gct gac gaa     144
Gly Pro Cys Lys Met Ile Ala Pro Ile Leu Asp Glu Ile Ala Asp Glu
35                  40                  45 tat cag ggc aaa ctg acc gtt gca aaa ctg aac atc gat caa aac cct     192
Tyr Gln Gly Lys Leu Thr Val Ala Lys Leu Asn Ile Asp Gln Asn Pro
50                  55                  60 ggc act gcg ccg aaa tat ggc atc cgt ggt atc ccg act ctg ctg ctg     240
Gly Thr Ala Pro Lys Tyr Gly Ile Arg Gly Ile Pro Thr Leu Leu Leu
65                  70                  75                  80 ttc aaa aac ggt gaa gtg gcg gca acc aaa gtg ggt gca ctg tct aaa     288
Phe Lys Asn Gly Glu Val Ala Ala Thr Lys Val Gly Ala Leu Ser Lys
            85                  90                  95 ggt cag ttg aaa gag ttc ctc gac gct aac ctg gcg                     324
Gly Gln Leu Lys Glu Phe Leu Asp Ala Asn Leu Ala
100                 105

<210> SEQ ID NO 48
<211> LENGTH: 108
<212> TYPE: PRT
<213> ORGANISM: Escherichia coli

<400> SEQUENCE: 48

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
35                  40                  45

Tyr Gln Gly Lys Leu Thr Val Ala Lys Leu Asn Ile Asp Gln Asn Pro
50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
            85                  90                  95

Gly Gln Leu Lys Glu Phe Leu Asp Ala Asn Leu Ala
100                 105
```

```
-continued

<210> SEQ ID NO 49
<211> LENGTH: 63
<212> TYPE: DNA
<213> ORGANISM: Pseudomonas fluorescens
<220> FEATURE:
<221> NAME/KEY: CDS
<222> LOCATION: (1)...(63)

<400> SEQUENCE: 49 atg aga aac ctt ctt cga gga atg ctt gtc gtt att tgc tgt atg gca      48
Met Arg Asn Leu Leu Arg Gly Met Leu Val Val Ile Cys Cys Met Ala
1               5                   10                  15 ggg ata gcg gcg gcg                                                  63
Gly Ile Ala Ala Ala
20

<210> SEQ ID NO 50
<211> LENGTH: 21
<212> TYPE: PRT
<213> ORGANISM: Pseudomonas fluorescens

<400> SEQUENCE: 50

Met Arg Asn Leu Leu Arg Gly Met Leu Val Val Ile Cys Cys Met Ala
1               5                   10                  15

Gly Ile Ala Ala Ala
20
```

BACTERIAL LEADER SEQUENCES FOR INCREASED EXPRESSION

CROSS REFERENCE TO RELATED APPLICATION

This application claims the benefit of U.S. Provisional Application Ser. Nos. 60/887,476, filed Jan. 31, 2007 and 60/887,486, filed Jan. 31, 2007, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "339398_SequenceListing.txt", created on Jan. 17, 2008, and having a size of 28,000 bytes and is filed concurrently with the specification. The sequence listing contained in this ASCII formatted document is part of the specification and is herein incorporated by reference in its entirety.

FIELD OF THE INVENTION

This invention is in the field of protein production, particularly to the use of targeting polypeptides for the production of properly processed heterologous proteins.

BACKGROUND OF THE INVENTION

More than 150 recombinantly produced proteins and polypeptides have been approved by the U.S. Food and Drug Administration (FDA) for use as biotechnology drugs and vaccines, with another 370 in clinical trials. Unlike small molecule therapeutics that are produced through chemical synthesis, proteins and polypeptides are most efficiently produced in living cells. However, current methods of production of recombinant proteins in bacteria often produce improperly folded, aggregated or inactive proteins, and many types of proteins require secondary modifications that are inefficiently achieved using known methods.

One primary problem with known methods lies in the formation of inclusion bodies made of aggregated proteins in the cytoplasm, which occur when an excess amount of protein accumulates in the cell. Another problem in recombinant protein production is establishing the proper secondary and tertiary conformation for the expressed proteins. One barrier is that bacterial cytoplasm actively resists disulfide bonds formation, which often underlies proper protein folding (Derman et al. (1993) Science 262:1744-7). As a result, many recombinant proteins, particularly those of eukaryotic origin, are improperly folded and inactive when produced in bacteria.

Numerous attempts have been developed to increase production of properly folded proteins in recombinant systems. For example, investigators have changed fermentation conditions (Schein (1989) Bio/Technology, 7:1141-1149), varied promoter strength, or used overexpressed chaperone proteins (Hockney (1994) Trends Biotechnol. 12:456-463), which can help prevent the formation of inclusion bodies.

An alternative approach to increase the harvest of properly folded proteins is to secrete the protein from the intracellular environment. The most common form of secretion of polypeptides with a signal sequence involves the Sec system. The Sec system is responsible for export of proteins with the N-terminal signal polypeptides across the cytoplasmic membranes (see Agarraberes and Dice (2001) Biochim Biophys Acta. 1513:1-24; Muller et al. (2001) Prog Nucleic Acid Res Mol. Biol. 66:107-157).

Strategies have been developed to excrete proteins from the cell into the supernatant. For example, U.S. Pat. No. 5,348,867; U.S. Pat. No. 6,329,172; PCT Publication No. WO 96/17943; PCT Publication No. WO 02/40696; and U.S. Application Publication 2003/0013150. Other strategies for increased expression are directed to targeting the protein to the periplasm. Some investigations focus on non-Sec type secretion (see for e.g. PCT Publication No. WO 03/079007; U.S. Publication No. 2003/0180937; U.S. Publication No. 2003/0064435; and, PCT Publication No. WO 00/59537). However, the majority of research has focused on the secretion of exogenous proteins with a Sec-type secretion system.

A number of secretion signals have been described for use in expressing recombinant polypeptides or proteins. See, for example, U.S. Pat. No. 5,914,254; U.S. Pat. No. 4,963,495; European Patent No. 0 177 343; U.S. Pat. No. 5,082,783; PCT Publication No. WO 89/10971; U.S. Pat. No. 6,156,552; U.S. Pat. Nos. 6,495,357; 6,509,181; 6,524,827; 6,528,298; 6,558,939; 6,608,018; 6,617,143; U.S. Pat. Nos. 5,595,898; 5,698,435; and 6,204,023; U.S. Pat. No. 6,258,560; PCT Publication Nos. WO 01/21662, WO 02/068660 and U.S. Application Publication 2003/0044906; U.S. Pat. No. 5,641,671; and European Patent No. EP 0 121 352.

Strategies that rely on signal sequences for targeting proteins out of the cytoplasm often produce improperly processed protein. This is particularly true for amino-terminal secretion signals such as those that lead to secretion through the Sec system. Proteins that are processed through this system often either retain a portion of the secretion signal, require a linking element which is often improperly cleaved, or are truncated at the terminus.

As is apparent from the above-described art, many strategies have been developed to target proteins to the periplasm of a host cell. However, known strategies have not resulted in consistently high yield of properly processed, active recombinant protein, which can be purified for therapeutic use. One major limitation in previous strategies has been the expression of proteins with poor secretion signal sequences in inadequate cell systems.

As a result, there is still a need in the art for improved large-scale expression systems capable of secreting and properly processing recombinant polypeptides to produce transgenic proteins in properly processed form.

SUMMARY OF THE INVENTION

The present invention provides improved compositions and processes for producing high levels of properly processed protein or polypeptide of interest in a cell expression system. In particular, the invention provides novel amino acid and nucleotide sequences for secretion signals derived from a bacterial organism. In one embodiment, the secretion signals of the invention include an isolated polypeptide with a sequence that is, or is substantially homologous to, a *Pseudomonas fluorescens* (*P. fluorescens*) secretion polypeptide selected from a mutant phosphate binding protein (pbp*), a protein disulfide isomerase A (dsbA), a protein disulfide isomerase C (dsbC), a CupA2, a CupB2, a CupC2, a NikA, a FlgI, a tetratricopeptide repeat family protein (ORF5550), a toluene tolerance protein (Ttg2C), or a methyl accepting chemotaxis protein (ORF8124) secretion signal, as well as biologically active variants, fragments, and derivatives thereof. In another embodiment, the secretion signals of the invention include an isolated polypeptide with a sequence that is, or is substantially homologous to, a *Bacillus coagulans* Bce secretion signal sequence. The nucleotide sequences encoding the signal sequences of the invention are useful in vectors and expression systems to promote targeting of an expressed protein or polypeptide of interest to the periplasm of Gram-negative bacteria or into the extracellular environment.

DNA constructs comprising the secretion signal sequences are useful in host cells to express recombinant proteins. Nucleotide sequences for the proteins of interest are operably linked to a secretion signal as described herein. The cell may express the protein in a periplasm compartment. In certain embodiments, the cell may also secrete expressed recombinant protein extracellularly through an outer cell wall. Host cells include eukaryotic cells, including yeast cells, insect cells, mammalian cells, plant cells, etc., and prokaryotic cells, including bacterial cells such as *P. fluorescens, E. coli*, and the like. Any protein of interest may be expressed using the secretion polypeptide leader sequences of the invention, including therapeutic proteins, hormones, a growth factors, extracellular receptors or ligands, proteases, kinases, blood proteins, chemokines, cytokines, antibodies and the like.

BRIEF DESCRIPTION OF THE FIGURES

FIG. 3 is an analysis after expression of dsbC-skp in *Pseudomonas fluorescens* after 0 and 24 hours in soluble (S) and insoluble (I) fractions for samples labeled 2B-2 (FIG. 3A) and 2B-4 (FIG. 3B). In FIG. 3B, bands 15, 17, and 19 were the unprocessed dsbC-skp protein in the insoluble fraction. Bands 16, 18, and 20 were the processed dsbC-skp in the insoluble fraction. Bands 11 and 13 were the processed dsbC-skp in the soluble fraction. Bands 12 and 14 were an unknown protein.

DETAILED DESCRIPTION

I. Overview

Figure 1:
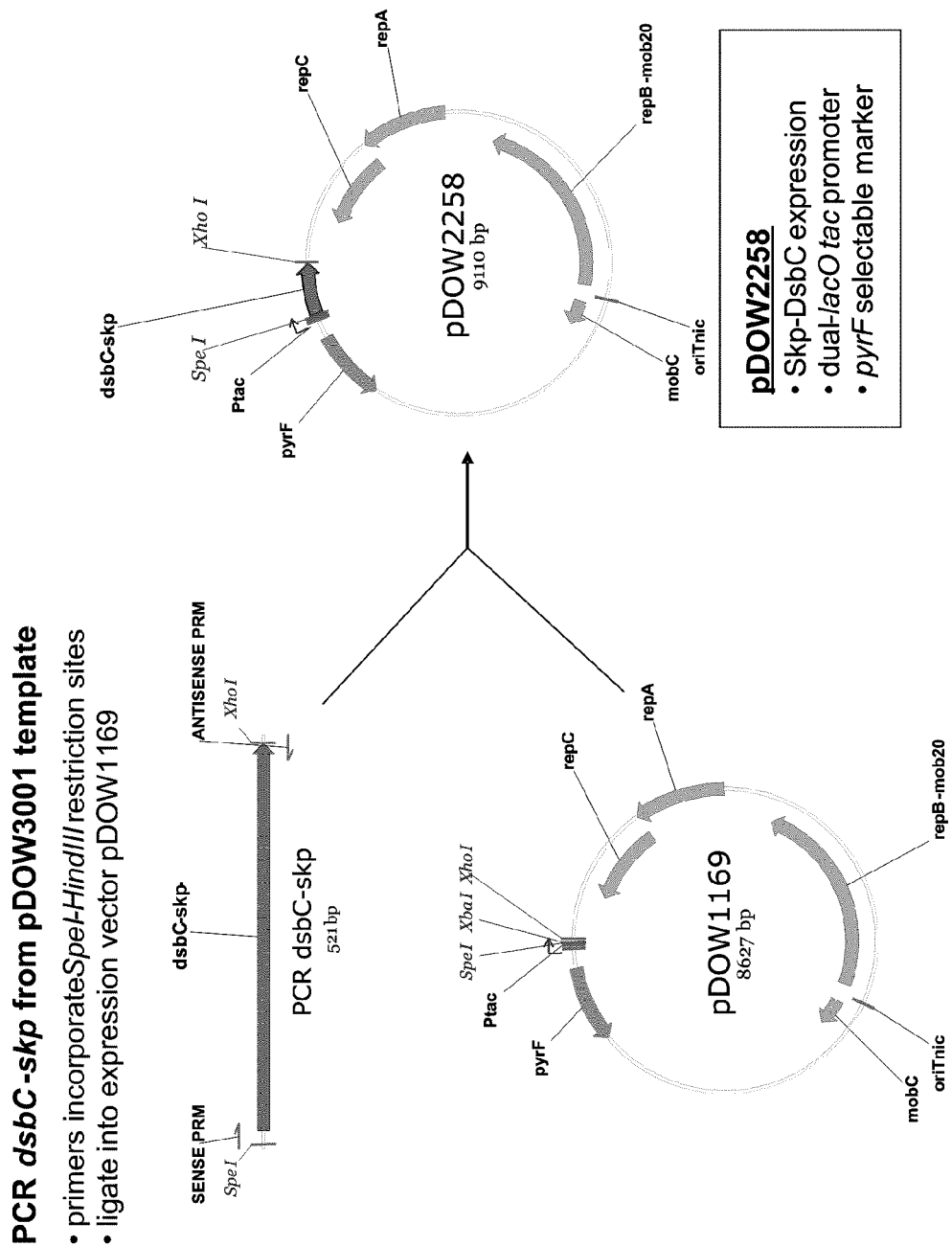
FIG. 1 depicts the expression construct for the dsbC SS-skp fusion protein.

Compositions and methods for producing high levels of properly processed polypeptides in a host cell are provided. In particular, novel secretion signals are provided which promote the targeting of an operably linked polypeptide of interest to the periplasm of Gram-negative bacteria or into the extracellular environment. For the purposes of the present invention, a "secretion signal," "secretion signal polypeptide," "signal peptide," or "leader sequence" is intended a peptide sequence (or the polynucleotide encoding the peptide sequence) that is useful for targeting an operably linked protein or polypeptide of interest to the periplasm of Gram-negative bacteria or into the extracellular space. The secretion signal sequences of the invention include the secretion polypeptides selected from pbp*, dsbA, dsbC, Bce, CupA2, CupB2, CupC2, NikA, FlgI, ORF5550, Ttg2C, and ORF8124 secretion signals, and fragments and variants thereof. The amino acid sequences for the secretion signals are set forth in SEQ ID NO:2, 4, 6, 8, 10, 12, 14, 16, 18, 20, 22, and 24. The corresponding nucleotide sequences are provided in SEQ ID NO:1, 3, 5, 7, 9, 11, 13, 15, 17, 19, 21, and 23, respectively. The invention comprises these sequences as well as fragments and variants thereof.

The methods of the invention provide improvements of current methods of production of recombinant proteins in bacteria that often produce improperly folded, aggregated or inactive proteins. Additionally, many types of proteins require secondary modifications that are inefficiently achieved using known methods. The methods herein increase the harvest of properly folded proteins by secreting the protein from the intracellular environment. In Gram-negative bacteria, a protein secreted from the cytoplasm can end up in the periplasmic space, attached to the outer membrane, or in the extracellular broth. The methods also avoid inclusion bodies, which are made of aggregated proteins. Secretion into the periplasmic space also has the well known effect of facilitating proper disulfide bond formation (Bardwell et al. (1994)

*Phosphate Microorg.* 270-5; Manoil (2000) Methods in *Enzymol.* 326: 35-47). Other benefits of secretion of recombinant protein include more efficient isolation of the protein; proper folding and disulfide bond formation of the transgenic protein, leading to an increase in the percentage of the protein in active form; reduced formation of inclusion bodies and reduced toxicity to the host cell; and increased percentage of the recombinant protein in soluble form. The potential for excretion of the protein of interest into the culture medium can also potentially promote continuous, rather than batch culture for protein production.

Gram-negative bacteria have evolved numerous systems for the active export of proteins across their dual membranes. These routes of secretion include, e.g.: the ABC (Type I) pathway, the Path/Fla (Type III) pathway, and the Path/Vir (Type IV) pathway for one-step translocation across both the plasma and outer membrane; the Sec (Type II), Tat, MscL, and Holins pathways for translocation across the plasma membrane; and the Sec-plus-fimbrial usher porin (FUP), Sec-plus-autotransporter (AT), Sec-plus-two partner secretion (TPS), Sec-plus-main terminal branch (MTB), and Tat-plus-MTB pathways for two-step translocation across the plasma and outer membranes. Not all bacteria have all of these secretion pathways.

Three protein systems (types I, III and IV) secrete proteins across both membranes in a single energy-coupled step. Four systems (Sec, Tat, MscL and Holins) secrete only across the inner membrane, and four other systems (MTB, FUP, AT and TPS) secrete only across the outer membrane.

In one embodiment, the signal sequences of the invention utilize the Sec secretion system. The Sec system is responsible for export of proteins with the N-terminal signal polypeptides across the cytoplasmic membranes (see, Agarraberes and Dice (2001) *Biochim Biophys Acta.* 1513:1-24; Muller et al. (2001) *Prog Nucleic Acid Res Mol. Biol.* 66: 107-157). Protein complexes of the Sec family are found universally in prokaryotes and eukaryotes. The bacterial Sec system consists of transport proteins, a chaperone protein (SecB) or signal recognition particle (SRP) and signal peptidases (SPase I and SPase II). The Sec transport complex in *E. coli* consists of three integral inner membrane proteins, SecY, SecE and SecG, and the cytoplasmic ATPase, SecA. SecA recruits SecY/E/G complexes to form the active translocation channel. The chaperone protein SecB binds to the nascent polypeptide chain to prevent it from folding and targets it to SecA. The linear polypeptide chain is subsequently transported through the SecYEG channel and, following cleavage of the signal polypeptide, the protein is folded in the periplasm. Three auxiliary proteins (SecD, SecF and YajC) form a complex that is not essential for secretion but stimulates secretion up to ten-fold under many conditions, particularly at low temperatures.

Proteins that are transported into the periplasm, i.e. through a type II secretion system, can also be exported into the extracellular media in a further step. The mechanisms are generally through an autotransporter, a two partner secretion system, a main terminal branch system or a fimbrial usher porin.

Of the twelve known secretion systems in Gram-negative bacteria, eight are known to utilize targeting signal polypeptides found as part of the expressed protein. These signal polypeptides interact with the proteins of the secretion systems so that the cell properly directs the protein to its appropriate destination. Five of these eight signal-polypeptide-based secretion systems are those that involve the Sec system. These five are referred to as involved in Sec-dependent cytoplasmic membrane translocation and their signal polypeptides operative therein can be referred to as Sec dependent secretion signals. One of the issues in developing an appropriate secretion signal is to ensure that the signal is appropriately expressed and cleaved from the expressed protein.

Signal polypeptides for the sec pathway generally consist of the following three domains: (i) a positively charged n-region, (ii) a hydrophobic h-region and (iii) an uncharged but polar c-region. The cleavage site for the signal peptidase is located in the c-region. However, the degree of signal sequence conservation and length, as well as the cleavage site position, can vary between different proteins.

A signature of Sec-dependent protein export is the presence of a short (about 30 amino acids), mainly hydrophobic amino-terminal signal sequence in the exported protein. The signal sequence aids protein export and is cleaved off by a periplasmic signal peptidase when the exported protein reaches the periplasm. A typical N-terminal Sec signal polypeptide contains an N-domain with at least one arginine or lysine residue, followed by a domain that contains a stretch of hydrophobic residues, and a C-domain containing the cleavage site for signal peptidases.

Bacterial protein production systems have been developed in which transgenic protein constructs are engineered as fusion proteins containing both a protein of interest and a secretion signal in an attempt to target the protein out of the cytoplasm.

*P. fluorescens* has been demonstrated to be an improved platform for production of a variety of proteins and several efficient secretion signals have been identified from this organism (see, U.S. Application Publication Number 20060008877, herein incorporated by reference in its entirety). *P. fluorescens* produces exogenous proteins in a correctly processed form to a higher level than typically seen in other bacterial expression systems, and transports these proteins at a higher level to the periplasm of the cell, leading to increased recovery of fully processed recombinant protein. Therefore, in one embodiment, the invention provides a method for producing exogenous protein in a *P. fluorescens* cell by expressing the target protein linked to a secretion signal.

The secretion signal sequences of the invention are useful in *Pseudomonas*. The Pseudomonads system offers advantages for commercial expression of polypeptides and enzymes, in comparison with other bacterial expression systems. In particular, *P. fluorescens* has been identified as an advantageous expression system. *P. fluorescens* encompasses a group of common, nonpathogenic saprophytes that colonize soil, water and plant surface environments. Commercial enzymes derived from *P. fluorescens* have been used to reduce environmental contamination, as detergent additives, and for stereoselective hydrolysis. *P. fluorescens* is also used agriculturally to control pathogens. U.S. Pat. No. 4,695,462 describes the expression of recombinant bacterial proteins in *P. fluorescens*. Between 1985 and 2004, many companies capitalized on the agricultural use of *P. fluorescens* for the production of pesticidal, insecticidal, and nematocidal toxins, as well as on specific toxic sequences and genetic manipulation to enhance expression of these. See, for example, PCT Application Nos. WO 03/068926 and WO 03/068948; PCT publication No. WO 03/089455; PCT Application No. WO 04/005221; and, U.S. Patent Publication Number 20060008877.

II. Compositions

A. Isolated Polypeptides

In one embodiment of the present invention, an isolated polypeptide is provided, wherein the isolated polypeptide is a novel secretion signal useful for targeting an operably linked protein or polypeptide of interest to the periplasm of Gram-negative bacteria or into the extracellular space. In one embodiment, the polypeptide has an amino acid sequence that is, or is substantially homologous to, a pbp*, dsbA, dsbC, Bce, CupA2, CupB2, CupC2, NikA, FlgI, ORF5550, Ttg2C, or ORF8124 secretion signal, or fragments or variants thereof. In another embodiment, this isolated polypeptide is a fusion protein of the secretion signal and a protein or polypeptide of interest.

In another embodiment, the polypeptide sequence is, or is substantially homologous to, the secretion signal polypeptide set forth in SEQ ID NO:2, 4, 6, 8, 10, 12, 14, 16, 18, 20, 22, or 24, or is encoded by the polynucleotide sequence set forth in SEQ ID NO:1, 3, 5, 7, 9, 11, 13, 15, 17, 19, 21, or 23. In another embodiment, the polypeptide sequence comprises at least amino acids 2-24 of SEQ ID NO:2, at least amino acids 2-22 of SEQ ID NO:4, at least amino acids 2-21 of SEQ ID NO:6, at least amino acids 2-33 of SEQ ID NO:8, at least amino acids 2-25 of SEQ ID NO:10, at least amino acids 2-24 of SEQ ID NO:12, at least amino acids 2-23 of SEQ ID NO:14, at least amino acids 2-21 of SEQ ID NO:16, at least amino acids 2-21 of SEQ ID NO:18, at least amino acids 2-21 of SEQ ID NO:20, at least amino acids 2-33 of SEQ ID NO:22, or at least amino acids 2-39 of SEQ ID NO:24. In yet another embodiment, the polypeptide sequence comprises a fragment of SEQ ID NO:2, 4, 6, 8, 10, 12, 14, 16, 18, 20, 22, or 24, which is truncated by 1, 2, 3, 4, 5, 6, 7, 8, 9, or 10 amino acids from the amino terminal but retains biological activity, i.e., secretion signal activity.

In one embodiment the amino acid sequence of the homologous polypeptide is a variant of a given original polypeptide, wherein the sequence of the variant is obtainable by replacing up to or about 30% of the original polypeptide's amino acid residues with other amino acid residue(s), including up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, provided that the variant retains the desired function of the original polypeptide. A variant amino acid with substantial homology will be at least about 70%, at least about 75%, at least about 80%, about 85%, about 90%, about 95%, about 96%, about 97%, about 98%, or at least about 99% homologous to the given polypeptide. A variant amino acid may be obtained in various ways including amino acid substitutions, deletions, truncations, and insertions of one or more amino acids of SEQ ID NO:2, 4, 6, 8, 10, 12, 14, 16, 18, 20, 22, or 24, including up to about 1, about 2, about 3, about 4, about 5, about 6, about 7, about 8, about 9, about 10, about 15, about 20, about 25, or more amino acid substitutions, deletions or insertions.

By "substantially homologous" or "substantially similar" is intended an amino acid or nucleotide sequence that has at least about 60% or 65% sequence identity, about 70% or 75% sequence identity, about 80% or 85% sequence identity, about 90%, about 91%, about 92%, about 93%, about 94%, about 95%, about 96%, about 97%, about 98% or about 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

For example, preferably, conservative amino acid substitutions may be made at one or more predicted, preferably nonessential amino acid residues. A "nonessential" amino acid residue is a residue that can be altered from the wild-type sequence of a secretion signal polypeptide without altering the biological activity, whereas an "essential" amino acid residue is required for biological activity. A "conservative amino acid substitution" is one in which the amino acid residue is replaced with an amino acid residue having a similar side chain. Families of conservative and semi-conservative amino acid residues are listed in Table 1.

TABLE 1

Similar Amino Acid Substitution Groups

| Conservative Groups (8) | Semi-Conservative Groups (7) |
| --- | --- |
| Arg, Lys | Arg, Lys, His |
| Asp, Gln | Asn, Asp, Gly, Gln |
| Asn, Glu | |
| Ile, Leu, Val | Ile, Leu, Val, Met, Phe |
| Ala, Gly | Ala, Gly, Pro, Ser, Thr |
| Ser, Thr | Ser, Thr, Tyr |
| Phe, Tyr | Phe, Trp, Tyr |
| Cys (non-cysteine), Ser | Cys (non-cysteine), Ser, Thr |

Variant proteins encompassed by the present invention are biologically active, that is they continue to possess the desired biological activity of the native protein; that is, retaining secretion signal activity. By "retains activity" is intended that the variant will have at least about 30%, at least about 50%, at least about 70%, at least about 80%, about 90%, about 95%, about 100%, about 110%, about 125%, about 150%, at least about 200% or greater secretion signal activity of the native protein.

B. Isolated Polynucleotides

The invention also includes an isolated nucleic acid with a sequence that encodes a novel secretion signal useful for targeting an operably linked protein or polypeptide of interest to the periplasm of Gram-negative bacteria or into the extracellular space. In one embodiment, the isolated polynucleotide encodes a polypeptide sequence substantially homologous to a pbp*, dsbA, dsbC, Bce, CupA2, CupB2, CupC2, NikA, FlgI, ORF5550, Ttg2C, or ORF8124 secretion signal polypeptide. In another embodiment, the present invention provides a nucleic acid that encodes a polypeptide sequence substantially homologous to at least amino acids 2-24 of SEQ ID NO:2, at least amino acids 2-22 of SEQ ID NO:4, at least amino acids 2-21 of SEQ ID NO:6, at least amino acids 2-33 of SEQ ID NO:8, at least amino acids 2-25 of SEQ ID NO:10, at least amino acids 2-24 of SEQ ID NO:12, at least amino acids 2-23 of SEQ ID NO:14, at least amino acids 2-21 of SEQ ID NO:16, at least amino acids 2-21 of SEQ ID NO:18, at least amino acids 2-21 of SEQ ID NO:20, at least amino acids 2-33 of SEQ ID NO:22, or at least amino acids 2-39 of SEQ ID NO:24, or provides a nucleic acid substantially homologous to SEQ ID NO:1, 3, 5, 7, 9, 11, 13, 15, 17, 19, 20, 21, or 23, including biologically active variants and fragments thereof. In another embodiment, the nucleic acid sequence is at least about 60%, at least about 65%, at least about 70%, about 75%, about 80%, about 85%, about 90%, about 95%, about 96%, about 97%, about 98%, or at least about 99% identical to the sequence of SEQ ID NO:1, 3, 5, 7, 9, 11, 13, 15, 17, 19, 20, 21, or 23. In another embodiment, the nucleic acid encodes a polypeptide that is at least about 70%, at least about 75%, at least about 80%, about 85%, about 90%, about 95%, about 96%, about 97%, about 98%, or at least about 99% identical to the amino acid sequence of SEQ ID NO:2, 4, 6, 8, 10, 12, 14, 16, 18, 20, 22, or 24.

Preferred secretion signal polypeptides of the present invention are encoded by a nucleotide sequence substantially homologous to the nucleotide sequences of SEQ ID NO:1 or 3. Using methods such as PCR, hybridization, and the like, corresponding secretion signal polypeptide sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). Variant nucleotide sequences also include synthetically derived nucleotide sequences that have been generated, for example, by using site-directed mutagenesis but which still encode the secretion signal polypeptides disclosed in the present invention as discussed infra. Variant secretion signal polypeptides encompassed by the present invention are biologically active, that is, they continue to possess the desired biological activity of the native protein, that is, retaining secretion signaling activity. By "retains activity" is intended that the variant will have at least about 30%, at least about 50%, at least 70%, at least about 80%, at least about 85%, at least about 90%, at least about 95%, about 96%, about 97%, about 98%, at least about 99% or greater of the activity of the native secretion signal polypeptide. Methods for measuring secretion signal polypeptide activity are discussed elsewhere herein.

The skilled artisan will further appreciate that changes can be introduced by mutation into the nucleotide sequences of the invention thereby leading to changes in the amino acid sequence of the encoded secretion signal polypeptides, without altering the biological activity of the secretion signal polypeptides. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

C. Nucleic Acid and Amino Acid Homology

Nucleic acid and amino acid sequence homology is determined according to any of various methods well known in the art. Examples of useful sequence alignment and homology determination methodologies include those described below.

Alignments and searches for similar sequences can be performed using the U.S. National Center for Biotechnology Information (NCBI) program, MegaBLAST (currently available at www.ncbi.nlm.nih.gov/BLAST/). Use of this program with options for percent identity set at, for example, 70% for amino acid sequences, or set at, for example, 90% for nucleotide sequences, will identify those sequences with 70%, or 90%, or greater sequence identity to the query sequence. Other software known in the art is also available for aligning and/or searching for similar sequences, e.g., sequences at least 70% or 90% identical to an information string containing a secretion signal sequence according to the present invention. For example, sequence alignments for comparison to identify sequences at least 70% or 90% identical to a query sequence can be performed by use of, e.g., the GAP, BEST-FIT, BLAST, FASTA, and TFASTA programs available in the GCG Sequence Analysis Software Package (available from the Genetics Computer Group, University of Wisconsin Biotechnology Center, 1710 University Avenue, Madison, Wis. 53705), with the default parameters as specified therein, plus a parameter for the extent of sequence identity set at the desired percentage. Also, for example, the CLUSTAL program (available in the PC/Gene software package from Intelligenetics, Mountain View, Calif.) may be used.

These and other sequence alignment methods are well known in the art and may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, Proc. Natl. Acad. Sci. USA 85:2444-48 (April 1988); the local homology method described in T. F. Smith & M. S. Waterman, in Adv. Appl. Math. 2:482-89 (1981) and in J. Molec. Biol. 147:195-97 (1981); the homology alignment method described in S. B. Needleman & C. D. Wunsch, J. Molec. Biol. 48(3):443-53 (March 1970); and the various methods described, e.g., by W. R. Pearson, in Genomics 11(3):635-50 (November 1991); by W. R. Pearson, in Methods Molec. Biol. 24:307-31 and 25:365-89 (1994); and by D. G. Higgins & P. M. Sharp, in Comp. Appl'ns in Biosci. 5:151-53 (1989) and in Gene 73(1): 237-44 (15 Dec. 1988).

Unless otherwise stated, GAP Version 10, which uses the algorithm of Needleman and Wunsch (1970) supra, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10. In various embodiments, the sequence comparison is performed across the entirety of the query or the subject sequence, or both.

D. Hybridization Conditions

In another aspect of the invention, a nucleic acid that hybridizes to an isolated nucleic acid with a sequence that encodes a polypeptide with a sequence substantially similar to a pbp*, dsbA, dsbC, Bce, CupA2, CupB2, CupC2, NikA, FlgI, ORF5550, Ttg2C, or ORF8124 secretion signal polypeptide is provided. In certain embodiments, the hybridizing nucleic acid will bind under high stringency conditions. In various embodiments, the hybridization occurs across substantially the entire length of the nucleotide sequence encoding the secretion signal polypeptide, for example, across substantially the entire length of one or more of SEQ ID NO:1, 3, 5, 7, 9, 11, 13, 15, 17, 19, 21, or 23. A nucleic acid molecule hybridizes to "substantially the entire length" of a secretion signal-encoding nucleotide sequence disclosed herein when the nucleic acid molecule hybridizes over at least 80% of the entire length of one or more of SEQ ID NO:1, 3, 5, 7, 9, 11, 13, 15, 17, 19, 21, or 23, at least 85%, at least 90%, or at least 95% of the entire length. Unless otherwise specified, "substantially the entire length" refers to at least 80% of the entire length of the secretion signal-encoding nucleotide sequence where the length is measured in contiguous nucleotides (e.g., hybridizes to at least 53 contiguous nucleotides of SEQ ID NO:3, at least 51 contiguous nucleotides of SEQ ID NO:5, at least 80 contiguous nucleotides of SEQ ID NO:7, etc.).

In a hybridization method, all or part of the nucleotide sequence encoding the secretion signal polypeptide can be used to screen cDNA or genomic libraries. Methods for construction of such cDNA and genomic libraries are generally known in the art and are disclosed in Sambrook and Russell, 2001. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known secretion signal polypeptide-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 10, at least about 15, at least about 16, 17, 18, 19, 20, or more consecutive nucleotides of a secretion signal polypeptide-encoding nucleotide sequence of the invention or a fragment or variant thereof. Methods for the preparation of probes for hybridization are generally known in the art and are disclosed in Sambrook and Russell, 2001, herein incorporated by reference.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the secretion signal polypeptide-encoding nucleotide sequence of the invention. Methods for the preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire secretion signal polypeptide-encoding nucleotide sequence disclosed herein, or one or more portions thereof, may be used as a probe capable of specifically hybridizing to corresponding nucleotide sequences and messenger RNAs encoding secretion signal polypeptides. To achieve specific hybridization under a variety of conditions, such probes include sequences that are unique and are preferably at least about 10 nucleotides in length, or at least about 15 nucleotides in length. Such probes may be used to amplify corresponding secretion signal polypeptide-encoding nucleotide sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 60° C., preferably about 68° C. Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 68° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

E Codon Usage

The nucleic acid sequences disclosed herein may be adjusted based on the codon usage of a host organism. Codon usage or codon preference is well known in the art. The selected coding sequence may be modified by altering the genetic code thereof to match that employed by the bacterial host cell, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari, Kisarazu, Chiba 292-0818 Japan) and available at www.kazusa.orjp/codon; and (2) the Genetic Codes tables available from the NCBI Taxonomy database at www.ncbi.nln.nih.gov/-Taxonomy/Utils/wprintgc.cgi?mode=c. For example, *Pseudomonas* species are reported as utilizing Genetic Code Translation Table 11 of the NCBI Taxonomy site, and at the Kazusa site as exhibiting the codon usage frequency of the table shown at www.kazusa.or.ip/codon/cgibin. It is recognized that the coding sequence for either the secretion signal polypeptide, the polypeptide of interest described elsewhere herein, or both, can be adjusted for codon usage.

F. Expression Vectors

Another embodiment of the present invention includes an expression vector which includes a nucleic acid that encodes a novel secretion polypeptide useful for targeting an operably linked protein or polypeptide of interest to the periplasm of Gram-negative bacteria or into the extracellular space. In one embodiment, the vector comprises a polynucleotide sequence that encodes a polypeptide that is substantially similar to a secretion signal polypeptide disclosed herein, operably linked to a promoter. Expressible coding sequences will be operatively attached to a transcription promoter capable of functioning in the chosen host cell, as well as all other required transcription and translation regulatory elements.

The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The vector will typically comprise one or more phenotypic selectable markers and an origin of replication to ensure maintenance of the vector and to, if desirable, provide amplification within the host. Suitable hosts for transformation in accordance with the present disclosure include various species within the genera *Pseudomonas*, and particularly preferred is the host cell strain of *P. fluorescens*.

In one embodiment, the vector further comprises a coding sequence for expression of a protein or polypeptide of interest, operably linked to the secretion signal disclosed herein. The recombinant proteins and polypeptides can be expressed from polynucleotides in which the target polypeptide coding sequence is operably linked to the leader sequence and transcription and translation regulatory elements to form a functional gene from which the host cell can express the protein or polypeptide. The coding sequence can be a native coding sequence for the target polypeptide, if available, but will more preferably be a coding sequence that has been selected, improved, or optimized for use in the selected expression host cell: for example, by synthesizing the gene to reflect the codon use bias of a host species. In one embodiment of the invention, the host species is a *P. fluorescens*, and the codon bias of *P. fluorescens* is taken into account when designing both the signal sequence and/or the protein or polypeptide sequence. The gene(s) are constructed within or inserted into one or more vector(s), which can then be transformed into the expression host cell.

Other regulatory elements may be included in a vector (also termed "expression construct"). Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitates identification, separation, purification, and/or isolation of an expressed polypeptide.

In another embodiment, the expression vector further comprises a tag sequence adjacent to the coding sequence for the secretion signal or to the coding sequence for the protein or polypeptide of interest. In one embodiment, this tag sequence allows for purification of the protein. The tag sequence can be an affinity tag, such as a hexa-histidine affinity tag. In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

A protein-encoding gene according to the present invention can include, in addition to the protein coding sequence, the following regulatory elements operably linked thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Starts of bacterial genes: estimating the reliability of computer predictions, Gene 234 (2):257-65 (8 Jul. 1999); and B. E. Suzek et al., A probabilistic method for identifying start codons in bacterial genomes, Bioinformatics 17(12): 1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a *Rhodococcus* species and its expression in *Escherichia coli*, Eur. J. Biochem. 181(3):563-70 (1989)(native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Transcription of the DNA encoding the proteins of the present invention is increased by inserting an enhancer sequence into the vector or plasmid. Typical enhancers are cis-acting elements of DNA, usually about from 10 to 300 bp in size that act on the promoter to increase its transcription. Examples include various *Pseudomonas* enhancers.

Generally, the recombinant expression vectors will include origins of replication and selectable markers permitting transformation of the host cell and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. The heterologous structural sequence is assembled in appropriate phase with translation initiation and termination sequences, and preferably, the secretion sequence capable of directing secretion of the translated polypeptide. Optionally the heterologous sequence can encode a fusion polypeptide including an N-terminal identification polypeptide imparting desired characteristics, e.g., stabilization or simplified purification of expressed recombinant product.

Vectors are known in the art for expressing recombinant proteins in host cells, and any of these may be used for expressing the genes according to the present invention. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1):11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1): 477-80 (January 1990); D. O. Wood et al., in J. Bact. 145(3): 1448-51 (March 1981); and R. Holtwick et al., in Microbiology 147(Pt 2):337-44 (February 2001).

Further examples of expression vectors that can be useful in a host cell comprising the secretion signal constructs of the invention include those listed in Table 2 as derived from the indicated replicons.

TABLE 2

Examples of Useful Expression Vectors

| Replicon | Vector(s) |
|---|---|
| PPS10 | PCN39, PCN51 |
| RSF1010 | PKT261-3 |
|  | PMMB66EH |
|  | PEB8 |
|  | PPLGN1 |
|  | PMYC1050 |
| RK2/RP1 | PRK415 |
|  | PJB653 |
| PRO1600 | PUCP |
|  | PBSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF110 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF110-based plasmid pTJS260 (see U.S. Pat. No. 5,169,760 to Wilcox), which carries a regulated tetracycline resistance marker and the replication and mobilization loci from the RSF 1010 plasmid. Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC4803 or a derivative thereof, is used as the expression vector.

The plasmid can be maintained in the host cell by inclusion of a selection marker gene in the plasmid. This may be an antibiotic resistance gene(s), where the corresponding antibiotic(s) is added to the fermentation medium, or any other type of selection marker gene known in the art, e.g., a prototrophy-restoring gene where the plasmid is used in a host cell that is auxotrophic for the corresponding trait, e.g., a biocatalytic trait such as an amino acid biosynthesis or a nucleotide biosynthesis trait, or a carbon source utilization trait.

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 3.

TABLE 3

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (ASM Press, Washington, D.C.); H. Schweizer (2001) Vectors to express foreign genes and techniques to monitor gene expression for Pseudomonads, Current Opinion in Biotechnology, 12:439-445; and R. Slater & R. Williams (2000) The Expression of Foreign DNA in Bacteria, in Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell may also be used to control expression of the transgene encoding the target polypeptide, e.g, a *Pseudomonas anthranilate* or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

By way of example, where a lac family promoter is utilized, a lacI gene can also be present in the system. The lacI gene, which is (normally) a constitutively expressed gene, encodes the Lac repressor protein (LacD protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-D-1-thiogalactopyranoside, also called "isopropylthiogalactoside").

For expression of a protein or polypeptide of interest, any plant promoter may also be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: *Genetic Engineering of Plants*, Kosuge et al., eds., pp. 211-227). In addition, virtually all promoters include additional upstream activating sequences or enhancers (Benoist and Chambon (1981) *Nature* 290:304-310; Gruss et al. (1981) *Proc. Nat. Acad. Sci.* 78:943-947; and Khoury and Gruss (1983) *Cell* 27:313-314) extending from around −100 bp to −1,000 bp or more upstream of the transcription initiation site.

G. Expression Systems

The present invention further provides an improved expression system useful for targeting an operably linked protein or polypeptide of interest to the periplasm of Gram-negative bacteria or into the extracellular space. In one embodiment, the system includes a host cell and a vector described above comprising a nucleotide sequence encoding a protein or polypeptide of interest operably linked to a secretion signal selected from the group consisting of a pbp*, dsbA, dsbC, Bce, CupA2, CupB2, CupC2, NikA, FlgI, ORF5550, Ttg2C, and ORF8124 secretion signal sequence, or a sequence that is substantially homologous to the secretion signal sequence disclosed herein as SEQ ID NO:1, 3, 5, 7, 9, 11, 13, 15, 17, 19, 20, 21, or 23, or a nucleotide sequence encoding SEQ ID NO:2, 4, 6, 8, 10, 12, 14, 16, 18, 20, 22, or 24. In some embodiments, no modifications are made between the signal sequence and the protein or polypeptide of interest. However, in certain embodiments, additional cleavage signals are incorporated to promote proper processing of the amino terminal of the polypeptide.

The secretion system can also include a fermentation medium, such as described below. In one embodiment, the system includes a mineral salts medium. In another embodiment, the system includes a chemical inducer in the medium.

The CHAMPION™ pET expression system provides a high level of protein production. Expression is induced from the strong T7lac promoter. This system takes advantage of the high activity and specificity of the bacteriophage T7 RNA polymerase for high level transcription of the gene of interest. The lac operator located in the promoter region provides tighter regulation than traditional T7-based vectors, improving plasmid stability and cell viability (Studier and Moffatt (1986) *J Molecular Biology* 189(1): 113-30; Rosenberg, et al. (1987) *Gene* 56(1): 125-35). The T7 expression system uses the T7 promoter and T7 RNA polymerase (T7 RNAP) for high-level transcription of the gene of interest. High-level expression is achieved in T7 expression systems because the T7 RNAP is more processive than native *E. coli* RNAP and is dedicated to the transcription of the gene of interest. Expression of the identified gene is induced by providing a source of T7 RNAP in the host cell. This is accomplished by using a BL21 *E. coli* host containing a chromosomal copy of the T7 RNAP gene. The T7 RNAP gene is under the control of the lacUV5 promoter which can be induced by IPTG. T7 RNAP is expressed upon induction and transcribes the gene of interest.

The pBAD expression system allows tightly controlled, titratable expression of protein or polypeptide of interest through the presence of specific carbon sources such as glucose, glycerol and arabinose (Guzman, et al. (1995) *J Bacteriology* 177(14): 4121-30). The pBAD vectors are uniquely designed to give precise control over expression levels. Heterologous gene expression from the pBAD vectors is initiated at the araBAD promoter. The promoter is both positively and negatively regulated by the product of the araC gene. AraC is a transcriptional regulator that forms a complex with L-arabinose. In the absence of L-arabinose, the AraC dimer blocks transcription. For maximum transcriptional activation two events are required: (i.) L-arabinose binds to AraC allowing transcription to begin. (ii.) The cAMP activator protein (CAP)-cAMP complex binds to the DNA and stimulates binding of AraC to the correct location of the promoter region.

The trc expression system allows high-level, regulated expression in *E. coli* from the trc promoter. The trc expression vectors have been optimized for expression of eukaryotic genes in *E. coli*. The trc promoter is a strong hybrid promoter derived from the tryptophane (trp) and lactose (lac) promoters. It is regulated by the lacO operator and the product of the lacIQ gene (Brosius, J. (1984) *Gene* 27(2): 161-72).

Transformation of the host cells with the vector(s) disclosed herein may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg2+ treatment, or other well known methods in the art. See, e.g., Morrison, *J. Bact.,* 132:349-351 (1977); Clark-Curtiss & Curtiss, *Methods in Enzymology,* 101:347-362 (Wu et al., eds, 1983), Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

H. Host Cell

In one embodiment the invention provides an expression system useful for targeting an operably linked protein or polypeptide of interest to the periplasm of Gram-negative bacteria or into the extracellular space. In one embodiment, this system utilizes a secretion signal peptide. In another embodiment, the expression system is a *P. fluorescens* expression system for expression of a protein comprising a secretion signal disclosed herein. This aspect of the invention is founded on the surprising discovery that *P. fluorescens* is capable of properly processing and targeting secretion signals from both *P. fluorescens* and non-*P. fluorescens* systems.

In this embodiment, the host cell can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens,* including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO$_2$; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236]; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212. [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21; [IFO 3081]; N; PYR; PW; D946-B83 [BU 2183; FERM-P 3328]; P-2563 [FERM-P 2894; IFO 13658]; IAM-1 126 [43F]; M-1; A506 [A5-06]; A505 [A5-05-1]; A526 [A5-26]; B69; 72; NRRL B-4290; PMW6 [NCIB 11615]; SC 12936; Al [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In one embodiment, the host cell can be any cell capable of producing a protein or polypeptide of interest, including a *P. fluorescens* cell as described above. The most commonly used systems to produce proteins or polypeptides of interest include certain bacterial cells, particularly *E. coli,* because of their relatively inexpensive growth requirements and potential capacity to produce protein in large batch cultures. Yeasts are also used to express biologically relevant proteins and polypeptides, particularly for research purposes. Systems include *Saccharomyces cerevisiae* or *Pichia pastoris.* These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell. In another embodiment, a multicellular organism is analyzed or is modified in the process, including but not limited to a transgenic organism. Techniques for analyzing and/or modifying a multicellular organism are generally based on techniques described for modifying cells described below.

In another embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans", a chapter of the On-Line Biology Book, provided by Dr M J Farabee of the Estrella Mountain Community College, Arizona, USA at the website www.emc-.maricotpa.edu/faculty/farabee/BIOBK/BioBookDiversity.

In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey, a primate or a human cell.

In one embodiment, the host cell can be a member of any of the bacterial taxa. The cell can, for example, be a member of any species of eubacteria. The host can be a member of any one of the taxa: Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Thermus (Thermales), or Verrucomicrobia. In a embodiment of a eubacterial host cell, the cell can be a member of any species of eubacteria, excluding Cyanobacteria.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gamma Proteobacterial host, the host will be member of any one of the taxa Aeromonadales, Alteromonadales, Enterobacteriales, Pseudomonadales, or Xanthomonadales; or a member of any species of the Enterobacteriales or Pseudomonadales. In one embodiment, the host cell can be of the order Enterobacteriales, the host cell will be a member of the family Enterobacteriaceae, or may be a member of any one of the genera *Erwinia, Escherichia,* or *Serratia*; or a member of the genus *Escherichia*. Where the host cell is of the order Pseudomonadales, the host cell may be a member of the family Pseudomonadaceae, including the genus *Pseudomonas*. Gamma Proteobacterial hosts include members of the species *Escherichia coli* and members of the species Pseudomonas fluorescens.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974)(The Williams & Wilkins Co., Baltimore, Md., USA)(hereinafter "Bergey (1974)"). Table 4 presents these families and genera of organisms.

TABLE 4

Families and Genera Listed in the Part,
"Gram-Negative Aerobic Rods and Cocci" (in Bergey (1974))

| Family I. Pseudomomonaceae | Gluconobacter |
| --- | --- |
| | Pseudomonas |
| | Xanthomonas |
| | Zoogloea |
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Family V. Halobacteriaceae | Halobacterium |
| | Halococcus |
| Other Genera | Acetobacter |
| | Alcaligenes |
| | Bordetella |
| | Brucella |
| | Francisella |
| | Thermus |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas,* the genus *Sphingomonas* (and the genus *Blastomonas,* derived therefrom), which was created by regrouping organisms belonging to (and previously called species of) the genus *Xanthomonas,* the genus *Acidomonas,* which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni,* respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae").

Consequently, in addition to those genera otherwise described herein, further

Proteobacterial genera falling within "Gram-negative Proteobacteria Subgroup 1" include: 1) *Azotobacter* group bacteria of the genus *Azorhizophilus;* 2)

Pseudomonadaceae family bacteria of the genera *Cellvibrio, Oligella,* and *Teredinibacter;* 3) Rhizobiaceae family bacteria of the genera *Chelatobacter, Ensifer, Liberibacter* (also called "*Candidatus Liberibacter*"), and *Sinorhizobium;* and 4) Methylococcaceae family bacteria of the genera *Methylobacter, Methylocaldum, Methylomicrobium, Methylosarcina,* and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beyerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera; Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600);

*Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffli* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas aspleni* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azoto-* formans; Pseudomonas brenneri; Pseudomonas cedrella; Pseudomonas corrugata (ATCC 29736); Pseudomonas extremorientalis; Pseudomonas fluorescens (ATCC 35858); Pseudomonas gessardii; Pseudomonas libanensis; Pseudomonas mandelii (ATCC 700871); Pseudomonas marginalis (ATCC 10844); Pseudomonas migulae; Pseudomonas mucidolens (ATCC 4685); Pseudomonas orientalis; Pseudomonas rhodesiae; Pseudomonas synxantha (ATCC 9890); Pseudomonas tolaasii (ATCC 33618); Pseudomonas veronji (ATCC 700474); Pseudomonas frederiksbergensis; Pseudomonas geniculata (ATCC 19374); Pseudomonas gingeri; Pseudomonas graminis; Pseudomonas grimontii; Pseudomonas halodenitrificans; Pseudomonas halophila; Pseudomonas hibiscicola (ATCC 19867); Pseudomonas huttiensis (ATCC 14670); Pseudomonas hydrogenovora; Pseudomonas jessenii (ATCC 700870); Pseudomonas kilonensis; Pseudomonas lanceolata (ATCC 14669); Pseudomonas lini; Pseudomonas marginata (ATCC 25417); Pseudomonas mephitica (ATCC 33665); Pseudomonas denitrificans (ATCC 19244); Pseudomonas pertucinogena (ATCC 190); Pseudomonas pictorum (ATCC 23328); Pseudomonas psychrophila; Pseudomonasfilva (ATCC 31418); Pseudomonas monteilii (ATCC 700476); Pseudomonas mosselii; Pseudomonas oryzihabitans (ATCC 43272); Pseudomonas plecoglossicida (ATCC 700383); Pseudomonas putida (ATCC 12633); Pseudomonas reactans; Pseudomonas spinosa (ATCC 14606); Pseudomonas balearica; Pseudomonas luteola (ATCC 43273); Pseudomonas stutzeri (ATCC 17588); Pseudomonas amygdali (ATCC 33614); Pseudomonas avellanae (ATCC 700331); Pseudomonas caricapapayae (ATCC 33615); Pseudomonas cichorii (ATCC 10857); Pseudomonas ficuserectae (ATCC 35104); Pseudomonas fuscovaginae; Pseudomonas meliae (ATCC 33050); Pseudomonas syringae (ATCC 19310); Pseudomonas viridiflava (ATCC 13223); Pseudomonas thermocarboxydovorans (ATCC 35961); Pseudomonas thermotolerans; Pseudomonas thivervalensis; Pseudomonas vancouverensis (ATCC 700688); Pseudomonas wisconsinensis; and Pseudomonas xiamenensis.

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following Pseudomonas species: Pseudomonas azotoformans; Pseudomonas brenneri; Pseudomonas cedrella; Pseudomonas corrugata; Pseudomonas extremorientalis; Pseudomonasfluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii; and Pseudomonas veronii.

Other suitable hosts include those classified in other parts of the reference, such as Gram (+) Proteobacteria. In one embodiment, the host cell is an E. coli. The genome sequence for E. coli has been established for E. coli MG1655 (Blattner, et al. (1997) The complete genome sequence of Escherichia coli K-12, Science 277(5331): 1453-74) and DNA microarrays are available commercially for E. coli K12 (MWG Inc, High Point, N.C.). E. coli can be cultured in either a rich medium such as Luria-Bertani (LB)(10 g/L tryptone, 5 g/L NaCl, 5 g/L yeast extract) or a defined minimal medium such as M9 (6 g/L Na$_2$HPO$_4$, 3 g/L KH$_2$PO$_4$, 1 g/L NH$_4$Cl, 0.5 g/L NaCl, pH 7.4) with an appropriate carbon source such as 1% glucose. Routinely, an over night culture of E. coli cells is diluted and inoculated into fresh rich or minimal medium in either a shake flask or a fermentor and grown at 37° C.

A host can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Any plant can be selected for the identification of genes and regulatory sequences. Examples of suitable plant targets for the isolation of genes and regulatory sequences would include but are not limited to alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the method are Arabidopsis, corn, wheat, soybean, and cotton.

III. Methods

The methods of the invention provide the expression of fusion proteins comprising a secretion signal polypeptide selected from a pbp*, dsbA, dsbC, Bce, CupA2, CupB2, CupC2, NikA, FlgI, ORF5550, Ttg2C, or ORF812 secretion signal. In one embodiment, the method includes a host cell expressing a protein of interest linked to a secretion signal of the invention. The methods include providing a host cell, preferably a P. fluorescens host cell, comprising a vector encoding a recombinant protein comprising the protein or polypeptide of interest operably linked to a secretion signal sequence disclosed herein, and growing the cell under conditions that result in expression of the protein or polypeptide. Alternatively, the method of expressing proteins or polypeptides using the identified secretion signals can be used in any given host system, including host cells of either eukaryotic or prokaryotic origin. The vector can have any of the characteristics described above. In one embodiment, the vector comprises a nucleotide sequence encoding the secretion signal polypeptides disclosed herein as SEQ ID NO:2, 4, 6, 8, 10, 12, 14, 16, 18, 20, 22, or 24, or variants and fragments thereof. In another embodiment, the vector comprises a nucleotide sequence comprising SEQ ID NO:1, 3, 5, 7, 9, 11, 13, 15, 17, 19, 20, 21, or 23.

In another embodiment, the host cell has a periplasm and expression of the secretion signal polypeptide results in the targeting of substantially all of the protein or polypeptide of interest to the periplasm of the cell. It is recognized that a small fraction of the protein expressed in the periplasm may actually leak through the cell membrane into the extracellular space; however, the majority of the targeted polypeptide would remain within the periplasmic space.

The expression may further lead to production of extracellular protein. The method may also include the step of purifying the protein or polypeptide of interest from the periplasm or from extracellular media. The secretion signal can be expressed in a manner in which it is linked to the protein and the signal-linked protein can be purified from the cell. Therefore, in one embodiment, this isolated polypeptide is a fusion protein of the secretion signal and a protein or polypeptide of interest. However, the secretion signal can also be cleaved from the protein when the protein is targeted to the periplasm. In one embodiment, the linkage between the secretion signal and the protein or polypeptide is modified to increase cleavage of the secretion signal.

The methods of the invention may also lead to increased production of the protein or polypeptide of interest within the host cell. The increased production alternatively can be an increased level of properly processed protein or polypeptide per gram of protein produced, or per gram of host protein. The increased production can also be an increased level of recoverable protein or polypeptide produced per gram of recombinant or per gram of host cell protein. The increased production can also be any combination of an increased level of total protein, increased level of properly processed protein, or increased level of active or soluble protein. In this embodiment, the term "increased" is relative to the level of protein or polypeptide that is produced, properly processed, soluble, and/or recoverable when the protein or polypeptide of interest is expressed in a cell without the secretion signal polypeptide of the invention.

An improved expression of a protein or polypeptide of interest can also refer to an increase in the solubility of the protein. The protein or polypeptide of interest can be produced and recovered from the cytoplasm, periplasm or extracellular medium of the host cell. The protein or polypeptide can be insoluble or soluble. The protein or polypeptide can include one or more targeting sequences or sequences to assist purification, as discussed supra.

The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or polypeptide can be precipitated by centrifugation at between 5,000 and 20,000×gravity when spun for 10-30 minutes in a buffer under physiological conditions. Insoluble proteins or polypeptides can be part of an inclusion body or other precipitated mass. The term "inclusion body" is meant to include any intracellular body contained within a cell wherein an aggregate of proteins or polypeptides has been sequestered.

The methods of the invention can produce protein localized to the periplasm of the host cell. In one embodiment, the method produces properly processed proteins or polypeptides of interest in the cell. In another embodiment, the expression of the secretion signal polypeptide may produce active proteins or polypeptides of interest in the cell. The method of the invention may also lead to an increased yield of proteins or polypeptides of interest as compared to when the protein is expressed without the secretion signal of the invention.

In one embodiment, the method produces at least 0.1 g/L protein in the periplasmic compartment. In another embodiment, the method produces 0.1 to 10 g/L periplasmic protein in the cell, or at least about 0.2, about 0.3, about 0.4, about 0.5, about 0.6, about 0.7, about 0.8, about 0.9 or at least about 1.0 g/L periplasmic protein. In one embodiment, the total protein or polypeptide of interest produced is at least 1.0 g/L, at least about 2 g/L, at least about 3 g/L, about 4 g/L, about 5 g/L, about 6 g/L, about 7 g/L, about 8 g/L, about 10 g/L, about 15 g/L, about 20 g/L, at least about 25 g/L, or greater. In some embodiments, the amount of periplasmic protein produced is at least about 5%, about 10%, about 15%, about 20%, about 25%, about 30%, about 40%, about 50%, about 60%, about 70%, about 80%, about 90%, about 95%, about 96%, about 97%, about 98%, about 99%, or more of total protein or polypeptide of interest produced.

In one embodiment, the method produces at least 0.1 g/L correctly processed protein. A correctly processed protein has an amino terminus of the native protein. In some embodiments, at least 50% of the protein or polypeptide of interest comprises a native amino terminus. In another embodiment, at least 60%, at least 70%, at least 80%, at least 90%, or more of the protein has an amino terminus of the native protein. In various embodiments, the method produces 0.1 to 10 g/L correctly processed protein in the cell, including at least about 0.2, about 0.3, about 0.4, about 0.5, about 0.6, about 0.7, about 0.8, about 0.9 or at least about 1.0 g/L correctly processed protein. In another embodiment, the total correctly processed protein or polypeptide of interest produced is at least 1.0 g/L, at least about 2 g/L, at least about 3 g/L, about 4 g/L, about 5 g/L, about 6 g/L, about 7 g/L, about 8 g/L, about 10 g/L, about 15 g/L, about 20 g/L, about 25 g/L, about 30 g/L, about 35 g/l, about 40 g/l, about 45 g/l, at least about 50 g/L, or greater. In some embodiments, the amount of correctly processed protein produced is at least about 5%, about 10%, about 15%, about 20%, about 25%, about 30%, about 40%, about 50%, about 60%, about 70%, about 80%, about 90%, about 95%, about 96%, about 97%, about 98%, at least about 99%, or more of total recombinant protein in a correctly processed form.

The methods of the invention can also lead to increased yield of the protein or polypeptide of interest. In one embodiment, the method produces a protein or polypeptide of interest as at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of protein or polypeptide in the host cell as a percentage of aggregate cellular protein. The determination of the percent total cell protein is well known in the art.

In a particular embodiment, the host cell can have a recombinant polypeptide, polypeptide, protein, or fragment thereof expression level of at least 1% tcp and a cell density of at least 40 g/L, when grown (i.e. within a temperature range of about 4° C. to about 55° C., including about 10° C., about 15° C., about 20° C., about 25° C., about 30° C., about 35° C., about 40° C., about 45° C., and about 50° C.) in a mineral salts medium. In a particularly preferred embodiment, the expression system will have a protein or polypeptide expression level of at least 5% tcp and a cell density of at least 40 g/L, when grown (i.e. within a temperature range of about 4° C. to about 55° C., inclusive) in a mineral salts medium at a fermentation scale of at least about 10 Liters.

In practice, heterologous proteins targeted to the periplasm are often found in the broth (see European Patent No. EP 0 288 451), possibly because of damage to or an increase in the fluidity of the outer cell membrane. The rate of this "passive" secretion may be increased by using a variety of mechanisms that permeabilize the outer cell membrane: colicin (Miksch et al. (1997) *Arch. Microbiol.* 167: 143-150); growth rate (Shokri et al. (2002) *App Miocrobiol Biotechnol* 58:386-392); TolIII overexpression (Wan and Baneyx (1998) *Protein Expression Purif:* 14: 13-22); bacteriocin release protein (Hsiung et al. (1989) *Bio/Technology* 7: 267-71), colicin A lysis protein (Lloubes et al. (1993) *Biochimie* 75: 451-8)

mutants that leak periplasmic proteins (Furlong and Sundstrom (1989) Developments in Indus. *Microbio.* 30: 141-8); fusion partners (Jeong and Lee (2002) *Appl. Environ. Microbio.* 68: 4979-4985); recovery by osmotic shock (Taguchi et al. (1990) *Biochimica Biophysica Acta* 1049: 278-85). Transport of engineered proteins to the periplasmic space with subsequent localization in the broth has been used to produce properly folded and active proteins in *E. coli* (Wan and Baneyx (1998) *Protein Expression Purif.* 14: 13-22; Simmons et al. (2002) *J. Immun. Meth.* 263: 133-147; Lundell et al. (1990) *J. Indust. Microbio.* 5: 215-27).

A. Production of Active Protein

In some embodiments, the protein can also be produced in an active form. The term "active" means the presence of biological activity, wherein the biological activity is comparable or substantially corresponds to the biological activity of a corresponding native protein or polypeptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or polypeptide using standard parameters. The determination of protein or polypeptide activity can be performed utilizing corresponding standard, targeted comparative biological assays for particular proteins or polypeptides. One indication that a protein or polypeptide of interest maintains biological activity is that the polypeptide is immunologically cross reactive with the native polypeptide.

The invention can also improve recovery of active protein or polypeptide of interest. Active proteins can have a specific activity of at least about 20%, at least about 30%, at least about 40%, about 50%, about 60%, at least about 70%, about 80%, about 90%, or at least about 95% that of the native protein or polypeptide that the sequence is derived from. Further, the substrate specificity ($k_{cat}/K_m$) is optionally substantially similar to the native protein or polypeptide. Typically, $k_{cat}/K_m$ will be at least about 30%, about 40%, about 50%, about 60%, about 70%, about 80%, at least about 90%, at least about 95%, or greater. Methods of assaying and quantifying measures of protein and polypeptide activity and substrate specificity ($k_{cat}/K_m$), are well known to those of skill in the art.

The activity of the protein or polypeptide of interest can be also compared with a previously established native protein or polypeptide standard activity. Alternatively, the activity of the protein or polypeptide of interest can be determined in a simultaneous, or substantially simultaneous, comparative assay with the native protein or polypeptide. For example, in vitro assays can be used to determine any detectable interaction between a protein or polypeptide of interest and a target, e.g. between an expressed enzyme and substrate, between expressed hormone and hormone receptor, between expressed antibody and antigen, etc. Such detection can include the measurement of calorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the *Pseudomonas* produced protein or polypeptide in comparison to physiological effects of the native protein or polypeptide, e.g. weight gain, change in electrolyte balance, change in blood clotting time, changes in clot dissolution and the induction of antigenic response. Generally, any in vitro or in vivo assay can be used to determine the active nature of the protein or polypeptide of interest that allows for a comparative analysis to the native protein or polypeptide so long as such activity is assayable. Alternatively, the proteins or polypeptides produced in the present invention can be assayed for the ability to stimulate or inhibit interaction between the protein or polypeptide and a molecule that normally interacts with the protein or polypeptide, e.g. a substrate or a component of the signal pathway that the native protein normally interacts. Such assays can typically include the steps of combining the protein with a substrate molecule under conditions that allow the protein or polypeptide to interact with the target molecule, and detect the biochemical consequence of the interaction with the protein and the target molecule.

Assays that can be utilized to determine protein or polypeptide activity are described, for example, in Ralph, P. J., et al. (1984) *J. Immunol.* 132:1858 or Saiki et al. (1981) *J. Immunol.* 127:1044, Steward, W. E. II (1980) *The Interferon Systems*. Springer-Verlag, Vienna and New York, Broxmeyer, H. E., et al. (1982) Blood 60:595, *Molecular Cloning: A Laboratory Manua"*, 2d ed., Cold Spring Harbor Laboratory Press, Sambrook, J., E. F. Fritsch and T. Maniatis eds., 1989, and *Methods in Enzymology: Guide to Molecular Cloning Techniques*, Academic Press, Berger, S. L. and A. R. Kimmel eds., 1987, A K Patra et al., *Protein Expr Purif,* 18(2): p/182-92 (2000), Kodama et al., *J. Biochem.* 99: 1465-1472 (1986); Stewart et al., *Proc. Nat'l. Acad. Sci.* USA 90: 5209-5213 (1993); (Lombillo et al., *J. Cell Biol.* 128:107-115 (1995); (Vale et al., *Cell* 42:39-50 (1985).

B. Cell Growth Conditions

The cell growth conditions for the host cells described herein can include that which facilitates expression of the protein of interest, and/or that which facilitates fermentation of the expressed protein of interest. As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly preferred.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in *J. Bact.* 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A preferred mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 5 below. The components can be added in the following order: first (NH$_4$)HPO$_4$, KH$_2$PO$_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose MgSO$_4$ and thiamine-HCL can be added. Control of pH at approximately 6.8 can be achieved using aqueous ammonia. Sterile distilled water can then be added to adjust the initial volume to 37l minus the glycerol stock (123 mL). The chemicals are commercially available from various suppliers, such as Merck. This media can allow for a high cell density cultivation (HCDC) for growth of *Pseudomonas* species and related bacteria. The HCDC can start as a batch process which is followed by a two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of. *Escherichia coli*, at controlled specific growth rate" *J Biotechnol:* 20(1) 17-27.

TABLE 5

Medium composition

| Component | Initial concentration |
|---|---|
| KH$_2$PO$_4$ | 13.3 g l$^{-1}$ |
| (NH$_4$)$_2$HPO$_4$ | 4.0 g l$^{-1}$ |
| Citric Acid | 1.7 g l$^{-1}$ |
| MgSO$_4$—7H$_2$O | 1.2 g l$^{-1}$ |
| Trace metal solution | 10 ml l$^{-1}$ |
| Thiamin HCl | 4.5 mg l$^{-1}$ |
| Glucose-H$_2$O | 27.3 g l$^{-1}$ |
| Antifoam Ucolub N115 | 0.1 ml l$^{-1}$ |
| Feeding solution | |
| MgSO$_4$—7H$_2$O | 19.7 g l$^{-1}$ |
| Glucose-H$_2$O | 770 g l$^{-1}$ |
| NH$_3$ | 23 g |
| Trace metal solution | |
| 6 g l$^{-1}$ Fe(III) citrate 1.5 g l$^{-1}$ MnCl$_2$—4H$_2$O 0.8 g l$^{-1}$ ZmCH$_2$COOI$_2$—2H$_2$O 0.3 g l$^{-1}$ H$_3$BO$_3$ 0.25 g l$^{-1}$ Na$_2$MoO$_4$—2H$_2$O 0.25 g l$^{-1}$ CoCl$_2$ 6H$_2$O 0.15 g l$^{-1}$ CuCl$_2$2H$_2$O 0.84 g l$^{-1}$ ethylene Dinitrilo-tetracetic acid Na$_2$ sah 2H$_2$O (Tritriplex III, Merck) | |

The expression system according to the present invention can be cultured in any fermentation format. For example, batch, fed-batch, semi-continuous, and continuous fermentation modes may be employed herein. Wherein the protein is excreted into the extracellular medium, continuous fermentation is preferred.

The expression systems according to the present invention are useful for transgene expression at any scale (i.e. volume) of fermentation. T hus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

An additional advantage in using *Pseudomonas fluorescens* in expressing secreted proteins includes the ability of *Pseudomonas fluorescens* to be grown in high cell densities compared to some other bacterial expression systems. To this end, *Pseudomonas fluorescens* expressions systems according to the present invention can provide a cell density of about 20 g/L or more. The Pseudomonasfluorescens expressions systems according to the present invention can likewise provide a cell density of at least about 70 g/L, as stated in terms of biomass per volume, the biomass being measured as dry cell weight.

In one embodiment, the cell density will be at least about 20 g/L. In another embodiment, the cell density will be at least about 25 g/L, about 30 g/L, about 35 g/L, about 40 g/L, about 45 g/L, about 50 g/L, about 60 g/L, about 70 g/L, about 80 g/L, about 90 g/L., about 100 g/L, about 110 g/L, about 120 g/L, about 130 g/L, about 140 g/L, about or at least about 150 g/L.

In another embodiments, the cell density at induction will be between about 20 g/L and about 150 g/L; between about 20 g/L and about 120 g/L; about 20 g/L and about 80 g/L; about 25 g/L and about 80 g/L; about 30 g/L and about 80 g/L; about 35 g/L and about 80 g/L; about 40 g/L and about 80 g/L; about 45 g/L and about 80 g/L; about 50 g/L and about 80 g/L; about 50 g/L and about 75 g/L; about 50 g/L and about 70 g/L; about 40 g/L and about 80 g/L.

C. Isolation of Protein or Polypeptide of Interest

To measure the yield, solubility, conformation, and/or activity of the protein of interest, it may be desirable to isolate the protein from the host cell and/or extracellular medium. The isolation may be a crude, semi-crude, or pure isolation, depending on the requirements of the assay used to make the appropriate measurements. The protein may be produced in the cytoplasm, targeted to the periplasm, or may be secreted into the culture or fermentation media. To release targeted proteins from the periplasm, treatments involving chemicals such as chloroform (Ames et al. (1984) *J. Bacteriol.,* 160: 1181-1183), guanidine-HCl, and Triton X-100 (Naglak and Wang (1990) *Enzyme Microb. Technol.,* 12: 603-611) have been used. However, these chemicals are not inert and may have detrimental effects on many recombinant protein products or subsequent purification procedures. Glycine treatment of *E. coli* cells, causing permeabilization of the outer membrane, has also been reported to release the periplasmic contents (Ariga et al. (1989) J. Ferm. Bioeng., 68: 243-246). The most widely used methods of periplasmic release of recombinant protein are osmotic shock (Nosal and Heppel (1966) *J. Biol. Chem.,* 241: 3055-3062; Neu and Heppel (1965) *J. Biol. Chem.,* 240:3685-3692), hen eggwhite (HEW)-lysozyme/ ethylenediamine tetraacetic acid (EDTA) treatment (Neu and Heppel (1964) *J. Biol. Chem.,* 239: 3893-3900; Witholt et al. (1976) *Biochim. Biophys. Acta,* 443: 534-544; Pierce et al. (1995) ICheme Research. Event, 2: 995-997), and combined HEW-lysozyme/osmotic shock treatment (French et al. (1996) *Enzyme and Microb. Tech.,* 19: 332-338). The French method involves resuspension of the cells in a fractionation buffer followed by recovery of the periplasmic fraction, where osmotic shock immediately follows lysozyme treatment.

Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al. (1994) *Veterinary Microbiol.,* 38: 307-314. For a general review of use of intracellular lytic enzyme systems to disrupt *E. coli,* see Dabora and Cooney (1990) in *Advances in Biochemical Engineering/Biotechnology,* Vol. 43, A. Fiechter, ed. (Springer-Verlag: Berlin), pp. 11-30.

Conventional methods for the recovery of proteins or polypeptides of interest from the cytoplasm, as soluble protein or refractile particles, involved disintegration of the bacterial cell by mechanical breakage. Mechanical disruption typically involves the generation of local cavitation in a liquid suspension, rapid agitation with rigid beads, sonication, or grinding of cell suspension (*Bacterial Cell Surface Techniques,* Hancock and Poxton (John Wiley & Sons Ltd, 1988), Chapter 3, p. 55).

HEW-lysozyme acts biochemically to hydrolyze the peptidoglycan backbone of the cell wall. The method was first developed by Zinder and Arndt (1956) *Proc. Natl. Acad. Sci. USA,* 42: 586-590, who treated *E. coli* with egg albumin (which contains HEW-lysozyme) to produce rounded cellular spheres later known as spheroplasts. These structures retained some cell-wall components but had large surface areas in which the cytoplasmic membrane was exposed. U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

Many different modifications of these methods have been used on a wide range of expression systems with varying degrees of success (Joseph-Liazun et al. (1990) *Gene,* 86: 291-295; Carter et al. (1992) *Bio/Technology,* 10: 163-167). Efforts to induce recombinant cell culture to produce lysozyme have been reported. EP 0 155 189 discloses a means for inducing a recombinant cell culture to produce lysozymes, which would ordinarily be expected to kill such host cells by means of destroying or lysing the cell wall structure.

U.S. Pat. No. 4,595,658 discloses a method for facilitating externalization of proteins transported to the periplasmic space of *E. coli*. This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. Asami et al. (1997) *J. Ferment. and Bioeng.,* 83: 511-516 discloses synchronized disruption of *E. coli* cells by T4 phage infection, and Tanji et al. (1998) *J. Ferment. and Bioeng.,* 85: 74-78 discloses controlled expression of lysis genes encoded in T4 phage for the gentle disruption of *E. coli* cells.

Upon cell lysis, genomic DNA leaks out of the cytoplasm into the medium and results in significant increase in fluid viscosity that can impede the sedimentation of solids in a centrifugal field. In the absence of shear forces such as those exerted during mechanical disruption to break down the DNA polymers, the slower sedimentation rate of solids through viscous fluid results in poor separation of solids and liquid during centrifugation. Other than mechanical shear force, there exist nucleolytic enzymes that degrade DNA polymer. In *E. coli*, the endogenous gene endA encodes for an endonuclease (molecular weight of the mature protein is approx. 24.5 kD) that is normally secreted to the periplasm and cleaves DNA into oligodeoxyribonucleotides in an endonucleolytic manner. It has been suggested that endA is relatively weakly expressed by *E. coli* (Wackernagel et al. (1995) *Gene* 154: 55-59).

In one embodiment, no additional disulfide-bond-promoting conditions or agents are required in order to recover disulfide-bond-containing identified polypeptide in active, soluble form from the host cell. In one embodiment, the transgenic polypeptide, polypeptide, protein, or fragment thereof has a folded intramolecular conformation in its active state. In one embodiment, the transgenic polypeptide, polypeptide, protein, or fragment contains at least one intramolecular disulfide bond in its active state; and perhaps up to 2, 4, 6, 8, 10, 12, 14, 16, 18, or 20 or more disulfide bonds.

The proteins of this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused with a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, *Protein Purification*: Principles and Practice, Springer-Verlag: N.Y. (1982); Deutscher, *Guide to Protein Purification*, Academic Press (1990); U.S. Pat. No. 4,511,503; S. Roe, *Protein Purification Techniques: A Practical Approach* (Practical Approach Series), Oxford Press (2001); D. Bollag, et al., Protein Methods, Wiley-Lisa, Inc. (1996); AK Patra et al., *Protein Expr Purif,* 18(2): p/182-92 (2000); and R. Mukhija, et al., *Gene* 165(2): p. 303-6 (1995). See also, for example, Ausubel, et al. (1987 and periodic supplements); Deutscher (1990) "Guide to Protein Purification," *Methods in Enzymology vol.* 182, and other volumes in this series; Coligan, et al. (1996 and periodic Supplements) *Current Protocols in Protein Science* Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) QIAexpress: The High Level Expression & Protein Purification System QUIAGEN, Inc., Chatsworth, Calif.

Detection of the expressed protein is achieved by methods known in the art and include, for example, radioimmunoassays, Western blotting techniques or immunoprecipitation.

Certain proteins expressed in this invention may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing reformation of immunologically and/or biologically active protein. Other suitable buffers are known to those skilled in the art.

The heterologously-expressed proteins present in the supernatant can be separated from the host proteins by standard separation techniques well known to those of skill in the art. For example, an initial salt fractionation can separate many of the unwanted host cell proteins (or proteins derived from the cell culture media) from the protein or polypeptide of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a protein or polypeptide of interest can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The protein or polypeptide of interest will pass through the membrane into the filtrate. The filtrate can then be chromatographed as described below.

The secreted proteins or polypeptides of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

D. Renaturation and Refolding

In some embodiments of the present invention, more than 50% of the expressed, transgenic polypeptide, polypeptide, protein, or fragment thereof produced can be produced in a renaturable form in a host cell. In another embodiment about 60%, 70%, 75%, 80%, 85%, 90%, 95% of the expressed protein is obtained in or can be renatured into active form.

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

The protein or polypeptide of interest can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM imidazole. Imidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in M H Lee et al., *Protein Expr. Purif.*, 25(1): p. 166-73 (2002), W. K. Cho et al., *J. Biotechnology*, 77(2-3): p. 169-78 (2000), Ausubel, et al. (1987 and periodic supplements), Deutscher (1990) "Guide to Protein Purification," *Methods in Enzymology* vol. 182, and other volumes in this series, Coligan, et al. (1996 and periodic Supplements) *Current Protocols in Protein Science* Wiley/Greene, NY, S. Roe, *Protein Purification Techniques: A Practical Approach* (Practical Approach Series), Oxford Press (2001); D. Bollag, et al., Protein Methods, Wiley-Lisa, Inc. (1996)

E. Proteins of Interest

The methods and compositions of the present invention are useful for producing high levels of properly processed protein or polypeptide of interest in a cell expression system. The protein or polypeptide of interest (also referred to herein as "target protein" or "target polypeptide") can be of any species and of any size. However, in certain embodiments, the protein or polypeptide of interest is a therapeutically useful protein or polypeptide. In some embodiments, the protein can be a mammalian protein, for example a human protein, and can be, for example, a growth factor, a cytokine, a chemokine or a blood protein. The protein or polypeptide of interest can be processed in a similar manner to the native protein or polypeptide. In certain embodiments, the protein or polypeptide does not include a secretion signal in the coding sequence. In certain embodiments, the protein or polypeptide of interest is less than 100 kD, less than 50 kD, or less than 30 kD in size. In certain embodiments, the protein or polypeptide of interest is a polypeptide of at least about 5, 10, 15, 20, 30, 40, 50 or 100 amino acids.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann.ac.il/cards), nucleotide sequence information can be also obtained from the EMBL Nucleotide Sequence Database (www.ebi.ac.uk/embl/) or the DNA Databanik of Japan (DDBJ, www.ddbi.nig.ac.ii/; additional sites for information on amino acid sequences include Georgetown's protein information resource website (www-nbrf. Georgetown. edu/pirl) and Swiss-Prot (au.expasy.org/sprot/sprot-top.html).

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; $\alpha$-1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated polypeptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-$\beta$, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or polypeptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., $\alpha$-FGF (FGF-1), $\beta$-FGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-$\alpha$, IFN-$\beta$, IFN-$\gamma$); leukemia inhibitory factor (LIF); ciliary neurotrophic factor (CNTF); oncostatin M; stem cell factor (SCF); transforming growth factors (e.g., TGF-$\alpha$, TGF-$\beta$1, TGF-$\beta$2, TGF-$\beta$3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-11MCAF, MCP-3, MCP-4, MDC/STCP-1/ABCD-1, MIP-1.quadrature., MIP-1.quadrature., MIP-2.quadrature./GRO.quadrature., MIP-3.quadrature./Exodus/LARC, MIP-3/Exodus-3/ELC, MIP-4/PARC/DC-CK1, PF-4, RANTES, SDF1, TARC, or TECK).

In one embodiment of the present invention, the protein of interest can be a multi-subunit protein or polypeptide. Multisubunit proteins that can be expressed include homomeric and heteromeric proteins. The multisubunit proteins may include two or more subunits, that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In another embodiment, the protein of interest can be a blood protein. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, polypeptides, and fragments thereof found primarily in the blood of mammals. The amino acid sequences for numerous blood proteins have been reported (see, S. S. Baldwin (1993) Comp. Biochem Physiol. 106b:203-218), including the amino acid sequence for human serum albumin (Lawn, L. M., et al. (1981) Nucleic Acids Research, 9:6103-6114.) and human serum transferrin (Yang, F. et al. (1984) Proc. Natl. Acad. Sci. USA 81:2752-2756).

In another embodiment, the protein of interest can be a recombinant enzyme or co-factor. The enzymes and co-factors expressed in this embodiment include but are not limited to aldolases, amine oxidases, amino acid oxidases, aspartases, B12 dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuramimidase; lactase, maltase, sucrase, and arabinofuranosidases.

In another embodiment, the protein of interest can be a single chain, Fab fragment and/or full chain antibody or fragments or portions thereof. A single-chain antibody can include the antigen-binding regions of antibodies on a single stably-folded polypeptide chain. Fab fragments can be a piece of a particular antibody. The Fab fragment can contain the antigen binding site. The Fab fragment can contain 2 chains: a light chain and a heavy chain fragment. These fragments can be linked via a linker or a disulfide bond.

The coding sequence for the protein or polypeptide of interest can be a native coding sequence for the target polypeptide, if available, but will more preferably be a coding sequence that has been selected, improved, or optimized for use in the selected expression host cell: for example, by synthesizing the gene to reflect the codon use bias of a *Pseudomonas* species such as *P. fluorescens* or other suitable organism. The gene(s) that result will have been constructed within or will be inserted into one or more vectors, which will then be transformed into the expression host cell. Nucleic acid or a polynucleotide said to be provided in an "expressible form" means nucleic acid or a polynucleotide that contains at least one gene that can be expressed by the selected expression host cell.

In certain embodiments, the protein of interest is, or is substantially homologous to, a native protein, such as a native mammalian or human protein. In these embodiments, the protein is not found in a concatameric form, but is linked only to a secretion signal and optionally a tag sequence for purification and/or recognition.

In other embodiments, the protein of interest is a protein that is active at a temperature from about 20 to about 42° C. In one embodiment, the protein is active at physiological temperatures and is inactivated when heated to high or extreme temperatures, such as temperatures over 65° C.

In one embodiment, the protein of interest is a protein that is active at a temperature from about 20 to about 42° C. and/or is inactivated when heated to high or extreme temperatures, such as temperatures over 65° C.; is, or is substantially homologous to, a native protein, such as a native mammalian or human protein and not expressed from nucleic acids in concatameric form; and the promoter is not a native promoter in *P. fluorescens* but is derived from another organism, such as *E. coli*.

In other embodiments, the protein when produced also includes an additional targeting sequence, for example a sequence that targets the protein to the extracellular medium. In one embodiment, the additional targeting sequence is operably linked to the carboxy-terminus of the protein. In another embodiment, the protein includes a secretion signal for an autotransporter, a two partner secretion system, a main terminal branch system or a fimbrial usher porin.

The following examples are offered by way of illustration and not by way of limitation.

EXPERIMENTAL EXAMPLES

Example 1

Identification of dsbC Leader Sequence

I. Materials and Methods

A. Construction of pDOW2258 Expression Plasmid

Standard recombinant DNA techniques were used in the construction of plasmid pDOW2258 used for the expression of the DsbC leader peptide-Skp fusion protein (FIG. 1).

A PCR amplification reaction was performed using Herculase Master Mix (Stratagene, #600610-51), primers RC-322 (5'-AATTACTAGTAGGAGGTACATTAT-GCGCTT-3', SEQ ID NO:25) and RC-323 (5'-TATACTC-GAGTTATTTAACCTGTTTCAGTA-3', SEQ ID NO:26), and template plasmid pDOW3001 (already containing the cloned dsbC leader-skp coding sequence fusion generated by SOE PCR) to amplify the 521 bp dsbC-skp coding sequence using the manufacturer's protocol. The PCR fragment was purified using the QIAQUICK® Gel Extraction Kit (Qiagen, #28704), digested with SpeI and XhoI restriction nucleases (New England Biolabs, R0133 and R0146), then ligated to the expression plasmid pDOW1169 (already digested with SpeI and XhoI) using T4 DNA ligase (New England Biolabs, M0202) according to the manufacturer's protocol. The ligation reaction was transformed into *P. fluorescens* DC454 (lsc::lacI$^{Q1}$ ΔpyrF) by electroporation, recovered in SOC-with-Soy medium and plated on selective medium (M9 glucose agar). Colonies were analyzed by restriction digestion of plasmid DNA (Qiagen, cat.#27106). Ten clones containing inserts were sequenced to confirm the presence of error-free dsbC-skp coding sequence. Plasmid from sequence confirmed isolates were designated pDOW2258.

B. Growth and Expression Analysis in Shake Flasks *P. fluorescens* strain DC454 (lsc::lacI$^{Q1}$ ΔpyrF) isolates containing pDOW2258 were analyzed by the standard Dow 1 L-scale shake-flask expression protocol. Briefly, seed cultures grown in M9 medium supplemented with 1% glucose and trace elements were used to inoculate 200 mL of defined minimal salts medium with 5% glycerol as the carbon source. Following an initial 24-hour growth phase, expression via the Ptac promoter was induced with 0.3 mM isopropyl-β-D-1-thiogalactopyranoside (IPTG).

Cultures were sampled at the time of induction (I0), at 24 hours after induction (I24), and at 48 hours after induction (I48). Cell density was measured by optical density at 600 nm ($OD_{600}$). The cell density was adjusted to $OD_{600}$=20, and aliquots of 100 μL were centrifuged at 14,000×rpm for 5 minutes and the supernatant was removed.

Soluble and insoluble fractions from shake flask samples were generated using EASYLYSE™ (Epicentre Technologies). The cell pellet was resuspended and diluted 1:4 in lysis buffer and incubated with shaking at room temperature for 30 minutes. The lysate was centrifuged at 14,000 rpm for 20 minutes (4° C.) and the supernatant removed. The supernatant was saved as the soluble fraction. Samples were mixed 1:1 with 2× Laemmli sample buffer containing β-mercaptoethanol (BioRad cat# 161-0737) and boiled for 5 minutes prior to loading 20 μL on a Bio-Rad Criterion 12% Bis-Tris gel (Bio-Rad cat# 45-0112 Lot# cx090505C2) and electrophoresis in 1×MES buffer (cat.# 161-0788 Lot# 210001188). Gels were stained with SIMPLYBLUE™ SafeStain (Invitrogen cat# LC6060) according to the manufacturer's protocol and imaged using the Alpha Innotech Imaging system.

C. N-terminal Sequencing Analysis

Soluble and insoluble fractions separated by SDS-PAGE were transferred to Sequencing grade PVDF membrane (Bio-Rad, cat.#162-0236) for 1.5 hours at 40V using 10 mM CAPS (2.21 g/L), pH 11 (with NaOH), and 10% methanol as the transfer buffer. The blot was stained in the staining solution (0.2% Commassie Brilliant Blue R-250, 40% methanol, 10% acetic acid) for ten seconds then immediately destained three times, ten seconds each. Protein bands of interest were cut out from the blot and sequenced using Edman degradation performed on a PROCISE® Protein Sequencer (model 494) from Applied Biosystems (Foster City, Calif.).

II. Results

Figure 2:
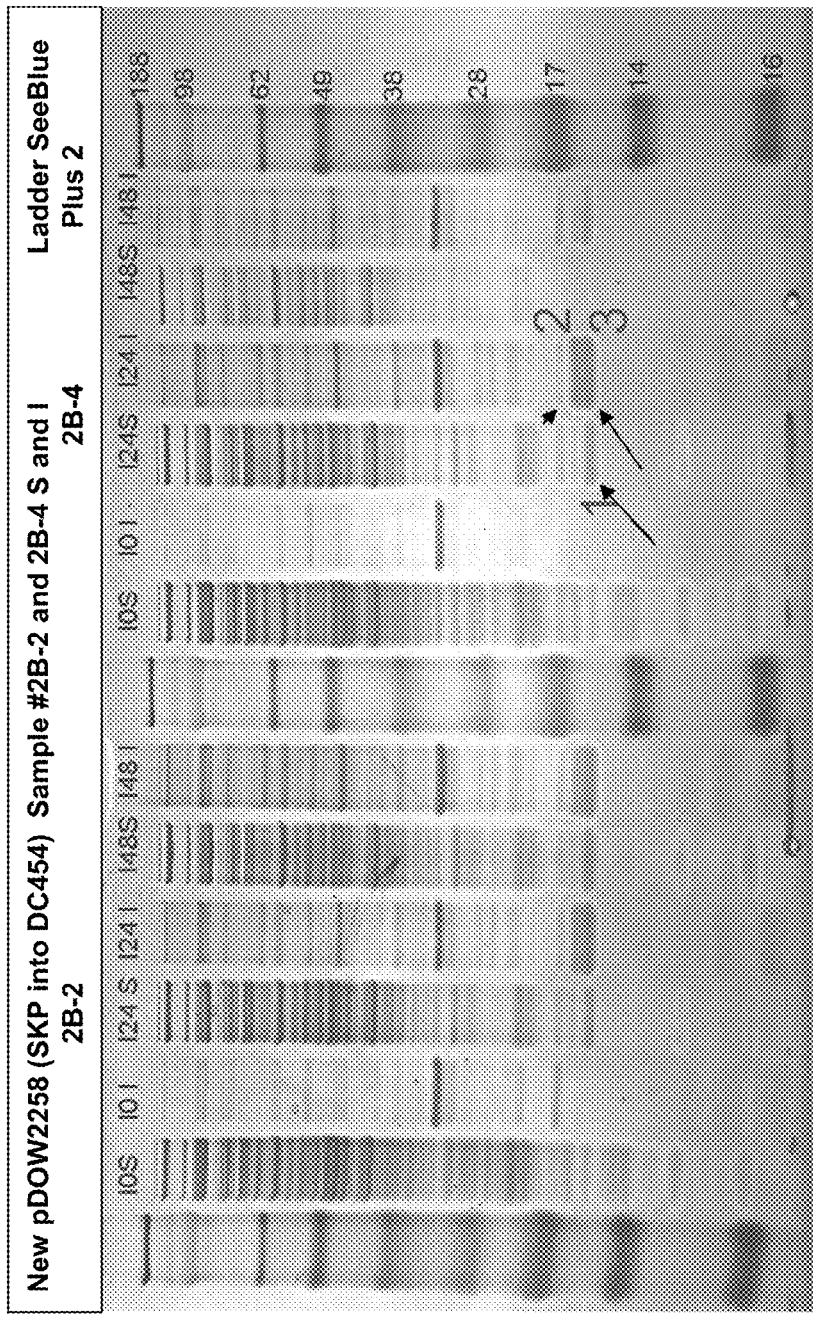
FIG. 2 shows expression of the Skp protein around 17 kDa (arrows). Bands labeled 2 and 3 were consistent with the Skp protein. Band 1 appears to have both DNA binding protein (3691) and Skp.

SDS-PAGE analysis confirmed significant accumulation of protein at the predicted molecular weight for Skp (~17 kDa) at both 24 hours (I24) and 48 hours (I48) post-induction in both the soluble and insoluble fractions (FIG. 2).

Figure 3A:
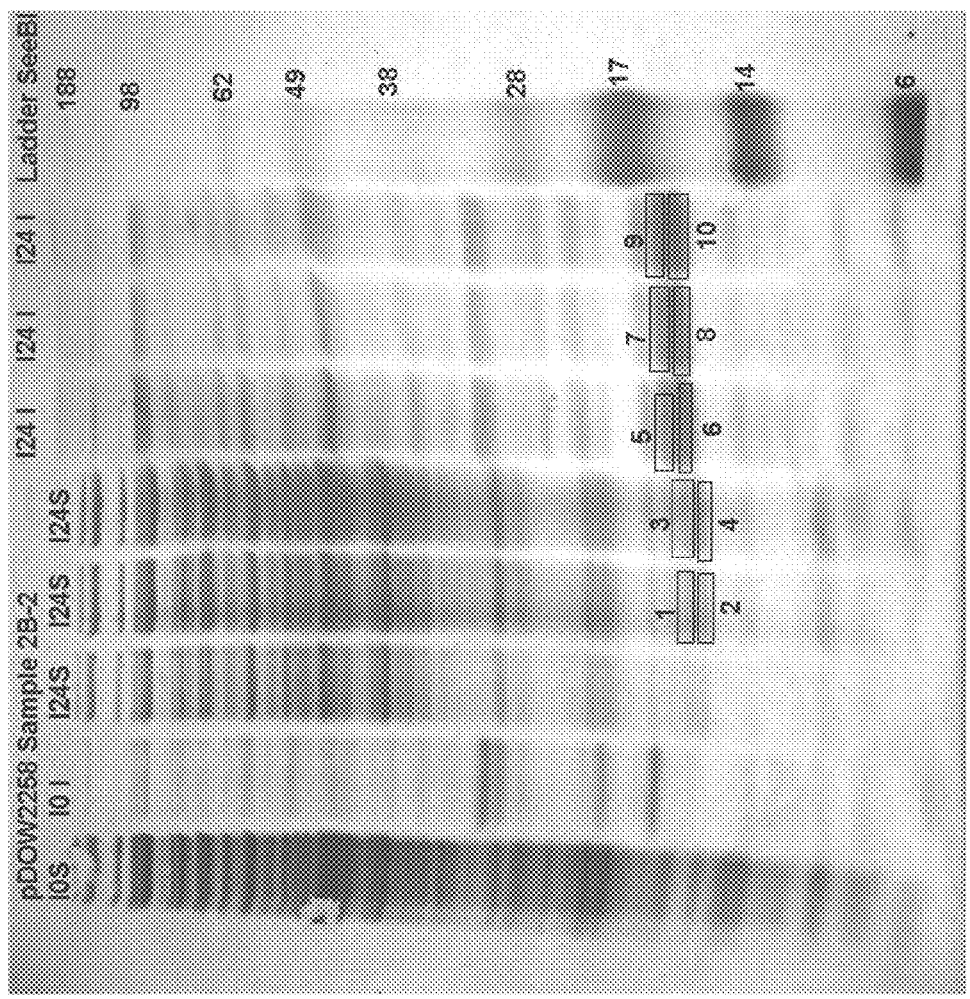
In FIG. 3A, bands 5, 7 and 9 were the unprocessed dsbC-skp protein in the insoluble fraction. Bands 6, 8, and 10 were the processed dsbC-skp in the insoluble fraction. Bands 1 and 3 were the processed dsbC-skp in the soluble fraction. Bands 2 and 4 were an unknown protein.
Figure 3B:
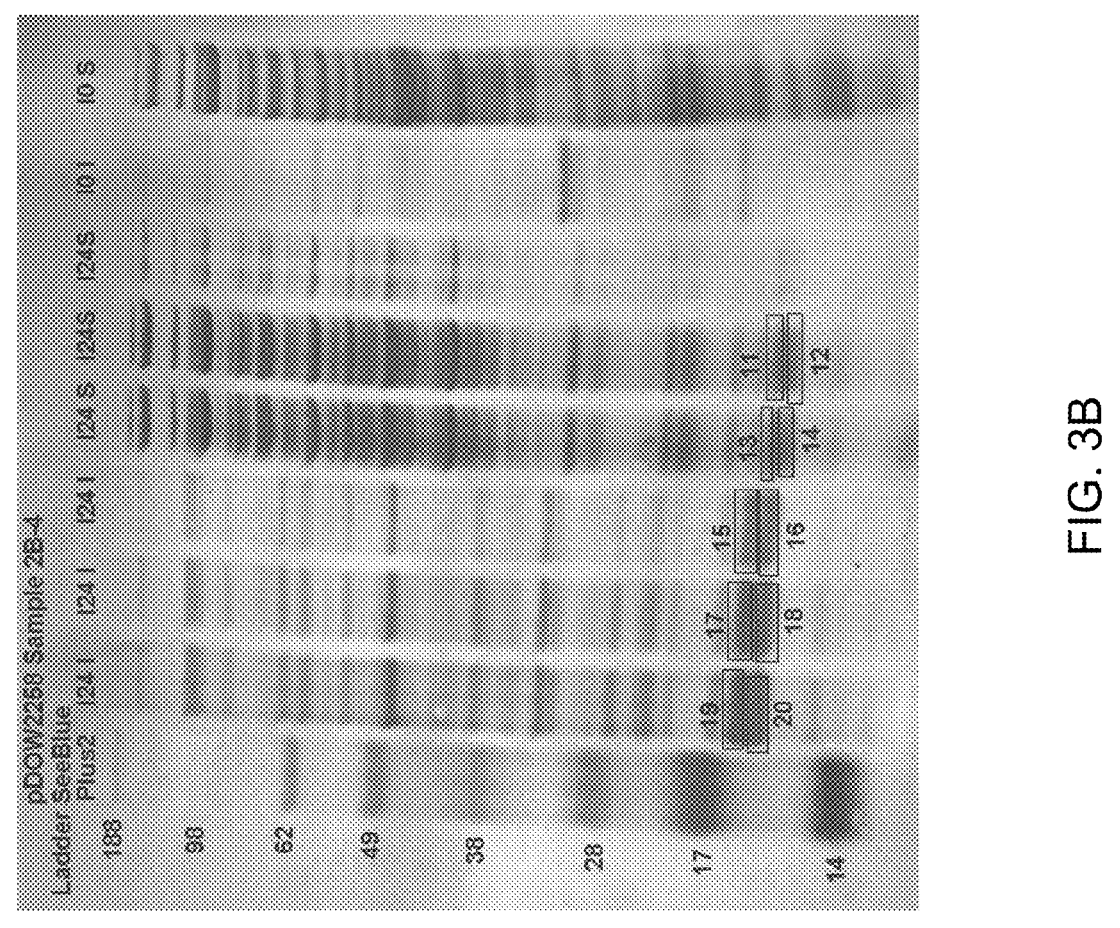
Figure 4:
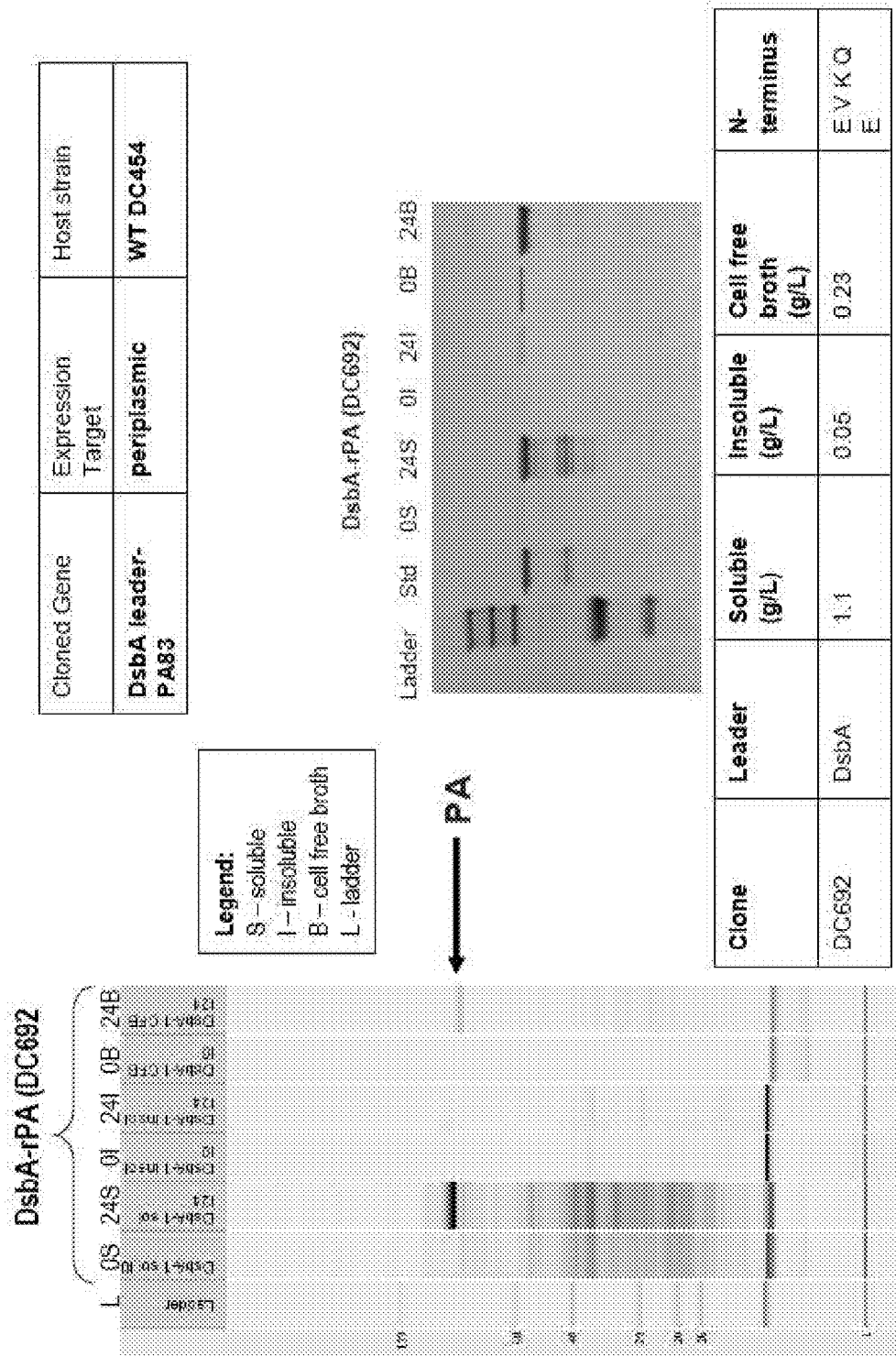
FIG. 4 shows a Western analysis of protein accumulation after expression of DC694 (dsbA-PA83). Accumulation of the soluble (S), insoluble (I), and cell free broth (B) at 0 and 24 hours was assessed by Western analysis.
Figure 5:
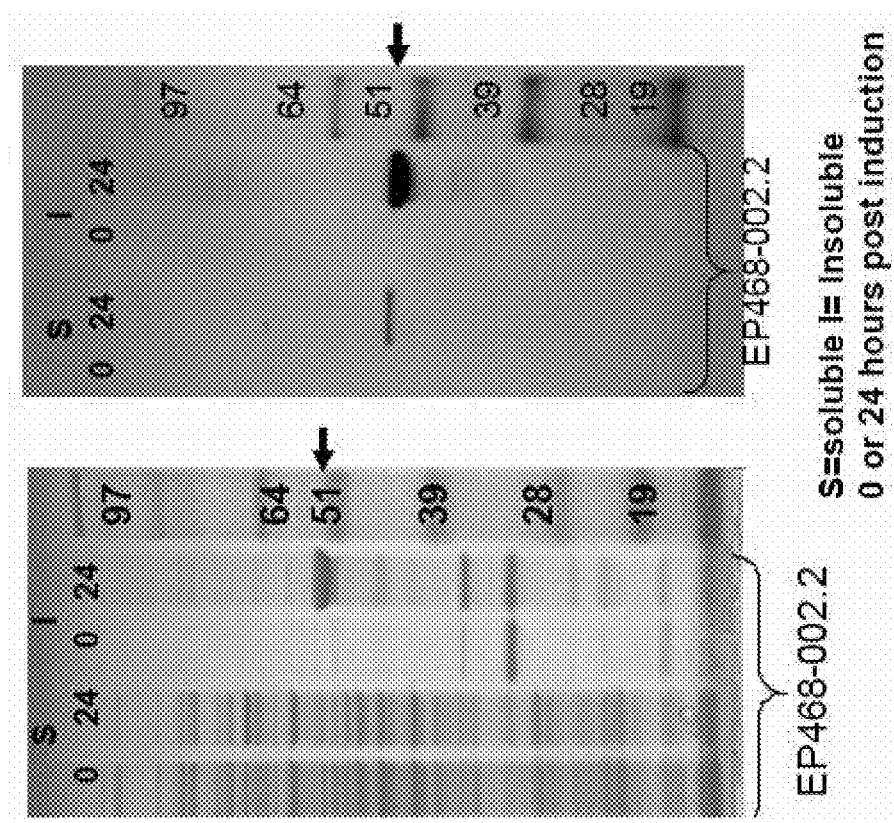
FIG. 5 shows a Western analysis of protein accumulation after expression of EP468-002.2 (dsbA). Accumulation of the soluble (S) and insoluble (I) protein at 0 and 24 hours after induction was assessed by Western analysis.

N-terminal sequencing analysis confirmed that the induced soluble band of expected size for Skp protein at I24 produced the first 5 amino acids of the predicted protein sequence for the processed form of DsbC-Skp (ADKIA, SEQ ID NO:27). The N-terminal analysis also showed that two bands that accumulated in the insoluble fraction at I24 produced both the processed and un-processed forms of DsbC-Skp. The higher molecular weight band produced the first 10 amino acids of the predicted protein sequence for the unprocessed from of DsbC-Skp (MRLTQIIAAA, SEQ ID NO:28) while the lower molecular weight band produced the first 10 amino acids of the predicted protein sequence for the processed form of the DsbC-Skp protein (ADKIAIVNMG, SEQ ID NO:29). See FIGS. 3A and 3B.

Example 2

Identification of pbp* Secretion Signal

I. Materials and Methods

A. Strains

DC206 (ΔpyrF, lsc::lacI$^{Q1}$) was constructed by PCR amplification of the E. coli lacI gene from pCN5 lacI (Schneider et al. 2005b) using primers incorporating the lacI$^{Q1}$ promoter mutation (Calos et al. 1980), and recombining the gene into the lsc (levan sucrase) locus of MB101 ΔpyrF (Schneider, Jenings et al. 2005b) by allele exchange.

B. Construction of Transposome to Screen for P. Fluorescens Signal Sequences

A transposome vector was engineered by inserting the kanR gene (encoding resistance to kanamycin) and a phoA reporter gene, which was missing the start codon and N-terminal signal sequence, between the vector-encoded transposase binding sites ("mosaic ends") in the transposome vector pMOD-2<MCS> (Epicentre Technologies). The 1.6 kB kanR gene was purified from pUC4-KIXX (Pharmacia) by restriction digestion with XhoI, then ligated into SalI-digested pMOD2<MCS> to form pDOW1245. The signal-sequence-less phoA gene was PCR-amplified from E. coli K12 (ATCC) with BamHI and XbaI sites added by the primers. After restriction digestion, the gene was ligated into BamHI- and XbaI-digested pDOW1245 to make pDOW1208. The linear transposome was prepared by restriction digestion of pDOW1208 with PshA1 and gel purification of the 3.3 kb mosaic-end-flanked fragment using Ultrafree DA (Amicon). After passage over a MicroBioSpin 6 column (Biorad), 30 ng was mixed with 4 units of transposase (Epicentre) and aliquots were electroporated into P. fluorescens MB 101.

C. Identification of Improved pbp Signal Sequence

A pbp-proinsulin-phoA expression plasmid was designed to fuse the pbp-proinsulin protein to a mature PhoA enzyme, so that accumulation of proinsulin-phoA in the periplasm could be measured and strains with improved accumulation could be selected by assaying for PhoA activity The fusion between the pbp signal sequence, human proinsulin, and phoA in pINS-008 was constructed by SOE PCR (Horton et al. 1990), using primers that overlap the coding sequence for the secretion leader and proinsulin, and for proinsulin and the mature form of PhoA (i.e. without the native secretion leader). The fusion was cloned under the control of the tac promoter in pDOW1169 (Schneider et al. 2005a; Schneider, Jenings et al. 2005b) which was restriction digested with SpeI and XhoI and treated with shrimp alkaline phosphatase, then ligated and electroporated into DC206, to form pINS-008. The proinsulin gene template was codon-optimized for expression in P. fluorescens and synthesized (DNA 2.0). The phoA gene was amplified from E. coli MG1655 genomic DNA. The colonies were screened on agar plates containing BCIP, a calorimetric indicator of alkaline phosphatase activity, with IPTG to induce expression of the pbp-proinsulin-phoA gene. Of the colonies that exhibited BCIP hydrolysis, one grew much larger than the others. This isolate was found to have a single C to T mutation in the region encoding the secretion peptide, causing a change from alanine to valine at amino acid 20 (A20V, SEQ ID NO:2; see Table 6).

Figure 6:
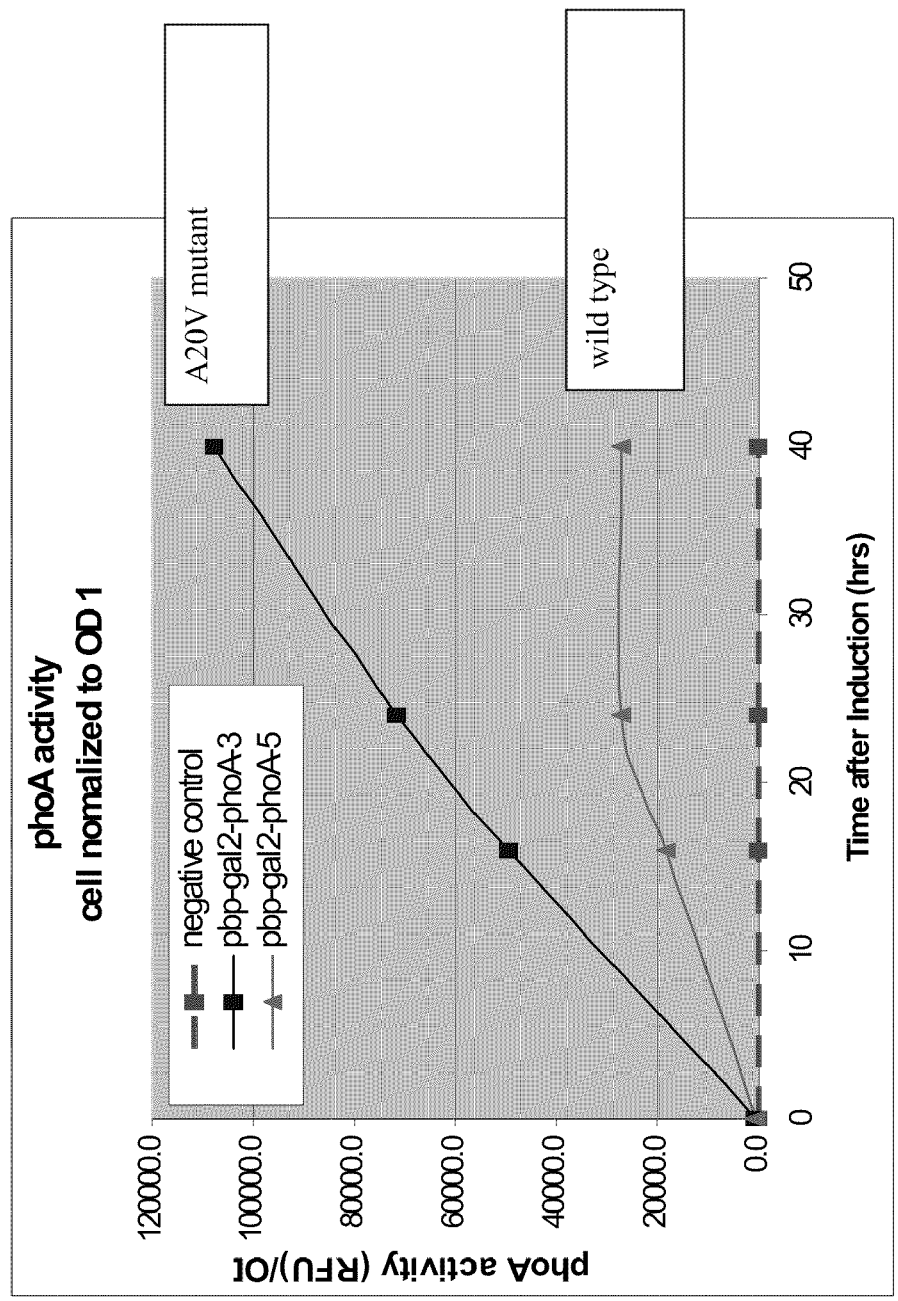
FIG. 6 demonstrates the alkaline phosphatase activity of the pINS-008-3 (pbp*) mutant compared to pINS-008-5 (wildtype pbp) secretion signal. Cell cultures were adjusted to 1 $OD_{600}$ unit, then PhoA activity was measured by adding 4-methylumbelliferone (MUP) and measuring fluorescent product formation at 10 min. The negative control contains MUP but no cells.
Figure 7:
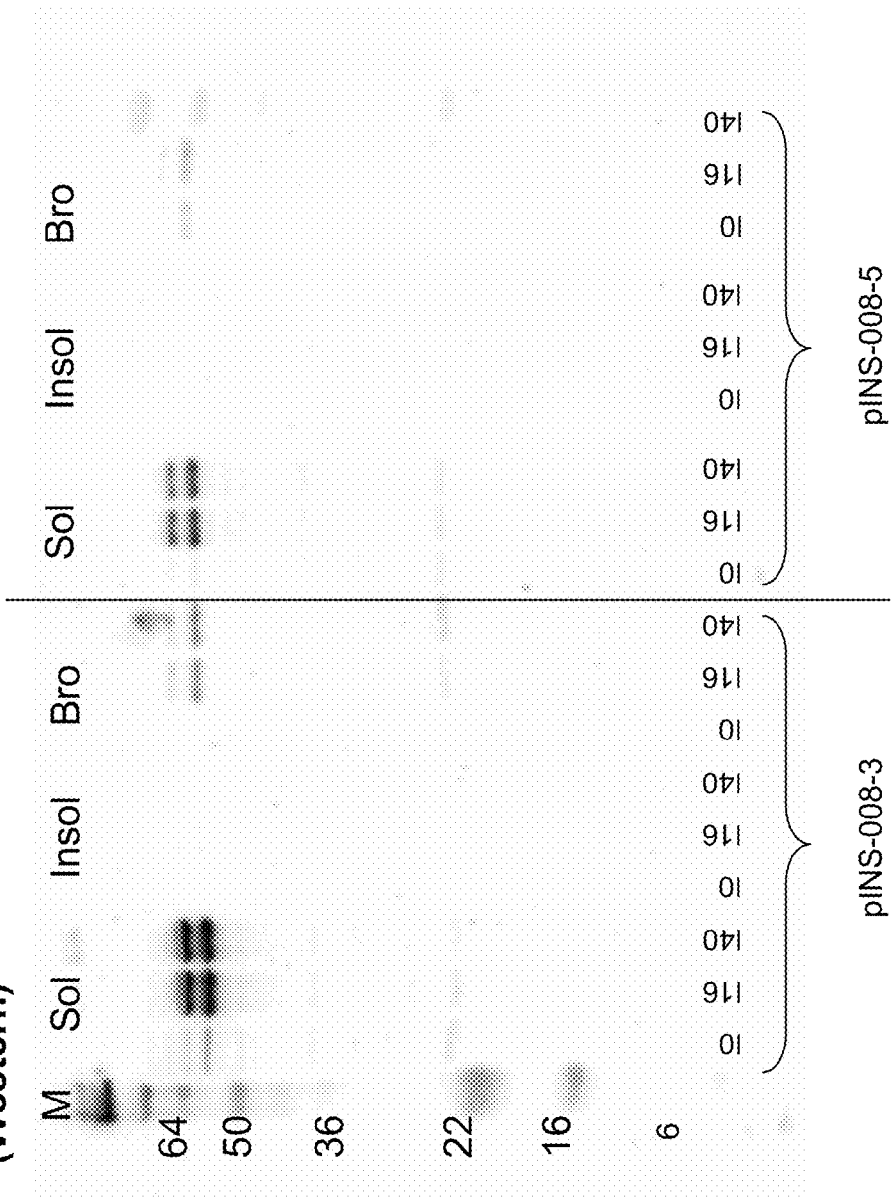
FIG. 7 shows a Western analysis of protein accumulation after expression of pINS-008-3 (pbp*) and pINS0008-5 (wildtype pbp). Accumulation of the proinsulin-phoA in the soluble (Sol), insoluble (Insol), and extracellular fraction (Bro) at I0, I16, and I40 hour was assessed by Western analysis. Aliquots of the culture were adjusted to 20 $OD_{600}$ units, separated by SDS-PAGE, transferred to a filter and visualized with an antibody to insulin (Chicken polyclonal, Abcam cat# ab14042).

The expression of the two strains was assessed by the standard shake flask protocol. The growth of both leveled off shortly after addition of the IPTG inducer. Alkaline phosphatase activity in the mutant pINS-008-3 strain was 3-4 times higher (FIG. 6), and accumulation of the (soluble) protein was higher (FIG. 7).

TABLE 6

Sec secretion signals identified in P. fluorescens

| Curated Protein Function | Abbreviation | Predicted signal sequence (signalP-HMM) | SEQ ID NO: | DNA sequence | SEQ ID NO: |
|---|---|---|---|---|---|
| pbp (signal sequence mutant) | pbp* | MKLKRLMAAMTF VAAGVATVNAVA | 2 | atgaaactgaaacgtttgatggcggcaa tgacttttgtcgctgctggcgttgcgacc gtcaacgcggtggcc | 1 |

TABLE 6-continued

Sec secretion signals identified in *P. fluorescens*

| Curated Protein Function | Abbreviation | Predicted signal sequence (signalP-HMM) | SEQ ID NO: | DNA sequence | SEQ ID NO: |
|---|---|---|---|---|---|
| porin E1 precursor | PO | MKKSTLAVAVTL GAIAQQAGA | 31 | atgaagaagtccaccttggctgtggctgt aacgttgggcgcaatcgcccagcaagc aggcgct | 30 |
| Outer membrane porin F | OP | MKLKNTLGLAIGS LIAATSFGVLA | 33 | atgaaactgaaaaacaccttgggcttgg ccattggttctcttattgccgctacttctttc ggcgttctggca | 32 |
| Periplasmic phosphate binding protein (pbp) | PB | MKLKRLMAAMTF VAAGVATANAVA | 35 | atgaaactgaaacgtttgatggcggcaa tgacttttgtcgctgctggcgttgcgacc gccaacgcggtggcc | 34 |
| azurin | AZ | MFAKLVAVSLLTL ASGQLLA | 37 | atgtttgccaaactcgttgctgtttccctg ctgactctggcgagcggccagttgcttg ct | 36 |
| rare lipoprotein B precursor | L | MIKRNLLVMGLA VLLSA | 39 | atgatcaaacgcaatctgctggttatggg ccttgccgtgctgttgagcgct | 38 |
| Lysine-arginine-ornithine-binding protein | LAO | MQNYKKFLLAAA VSMAFSATAMA | 41 | atgcagaactataaaaaattccttctggc cgcggccgtctcgatggcgttcagcgc cacggccatggca | 40 |
| Iron(III) binding protein | IB | MIRDNRLKTSLLR GLTLTLLSLTLLSP AAHS | 43 | atgatccgtgacaaccgactcaagacat cccttctgcgcggcctgaccctcaccct actcagcctgaccctgctctcgcccgcg gcccattct | 42 |

D. Genomic Sequencing

Genomic DNA was purified by the DNA Easy kit (Invitrogen) and 10 μg were used as template for sequencing with a transposon specific primer using 2× ABI PRISM BigDye Terminators v3.0 Cycle Kit (Applied Biosystems). The reactions were purified and loaded on the ABI PRISM 3100 Genetic Analyzer (Applied Biosystems) according to manufacturer's directions.

E. Cloning of Signal Sequence Coding Regions

Signal sequences were determined by SPScan software or as in (De et al. 1995). The results of these experiments have been disclosed in copending U.S. Patent Application Number 20060008877, filed Nov. 22, 2004. The outer membrane porin F (oprF) phosphate binding protein (pbp), porinE1 (porE), azurin, lipoprotein B and iron binding protein secretion leaders were amplified by polymerase chain reaction (PCR). The resulting PCR products were cloned into the pCRII Blunt TOPO vector and transformed into *E. coli* Top 10 cells (Invitrogen) according to the manufacturer's protocol. Resulting transformants were screened for correct insert by sequencing with M13 forward and M13 reverse primers. Positive clones were named as follows: oprF (pDOW1112), pbp (pDOW1113), porinE1 (pDOW1183), azurin (pDOW1180), lipoprotein B (pDOW1182), iron binding protein (pDOW1181).

F. Construction of gal2 scFv Clones for Secretion in *P. fluorescens*.

The OprF and pbp signal sequences were amplified to fuse to the Gal2 coding sequence at the +2 position using pDOW1112 or pDOW1113 as template. The gal2 coding sequence was amplified using pGal2 (Martineau et al. 1998) as template. The 837 bp SOE-PCR product was cloned into the pCR BLUNT II TOPO vector and sequence was confirmed. The scFv gene fused to signal sequence was excised from the TOPO vector with XbaI and SalI restriction enzymes and cloned into the SpeI and XhoI sites of pMYC1803 to produced pDOW1122 (oprF:gal2) and pDOW1123 (pbp: gal2) using standard cloning techniques (Sambrook et al. 2001). The resulting plasmids were transformed into DC191 selected on LB agar supplemented with 30 μg/mL tetracycline and 50 μg/mL kanamycin.

The porE signal sequence from pDOW1183 and fused by SOE-PCR to gal2 amplified from pDOW1123 and PCR products were purified by gel extraction. The resulting PCR product was cloned into PCRII Blunt TOPO and subsequently transformed into *E. coli* Top 10 cells according to manufacturer's instructions (Invitrogen). The resulting clones were sequenced and a positive clone (pDOW1185) selected for subcloning. pDOW1185 was restriction digested with SpeI and SalI, and the porE-gal2 fragment was gel purified. The purified fragment was ligated to SpeI-SalI digested pDOW1169 using T4 DNA ligase (NEB). The ligation mix was transformed into electrocompetent DC454 and selected on M9 1% glucose agar plates. Transformants were screened by restriction digestion of plasmid DNA using SpeI and SalI. A positive clone was isolated and stocked as pDOW1186.

Signal sequences of azurin, iron binding protein and lipB were amplified from clones pDOW1180, pDOW1181 and pDOW1182, respectively. The gal2 gene was amplified from pDOW1123 using appropriate primers to fuse to each secretion leader, and resultant PCR products were isolated and fused by SOE-PCR as described above. The SOE-PCR products were cloned into pCR-BLUNT II TOPO, the resultant clones were sequenced and positive clones for each fusion were subcloned into pDOW1169 as described above.

G. Construction of a *P. fluorescens* Secretion Vector with C-Terminal Histidine Tag A clone containing an insert with the pbp secretion leader, MCS with C-terminal His tag, and rrn T1T2 transcriptional terminators was synthesized by DNA 2.0 (pJ5:G03478). The 450 bp secretion cassette was isolated by restriction digestion with SpeI and NdeI and gel purified. The fragment was ligated to pDOW1219 (derived from pMYC 1803 (Shao et al. 2006)) digested with the same enzymes. The ligation products were transformed into chemically competent *E. coli* JM109. Plasmid DNA was prepared and screened for insert by PCR using vector specific primers. The resultant plasmid was sequence confirmed and named pDOW3718. Electrocompetent *P. fluorescens* DC454 was then transformed with the plasmid and selected on LB agar supplemented with 250 μg/mL uracil and 30 μg/mL tetracycline.

Open reading frames encoding human proteins were amplified using templates from the human ORFeome collection (Invitrogen). PCR products were restriciton digested with NheI and XhoI, and. then ligated to NheI-XhoI digested pDOW3718. Ligation products were subsequently transformed into electrocompetent *P. fluorescens* DC454 and transformants selected on LB agar supplemented with 250 μg/mL uracil and 30 μg/mL tetracycline. Positive clones were sequenced to confirm insert sequence.

H. Construction of *E. coli* Secretion Clones

Human ORFs were amplified as above, except that primers were designed with an NcoI site on the 5' primer and XhoI on the 3'primer. PCR products were restriction digested with NcoI and XhoI (NEB), then purified using Qiaquick Extraction kit (Qiagen) The digested products were ligated to NcoI-XhoI digested pET22b (Novagen) using T4 DNA ligase (NEB), and the ligation products were transformed into chemically competent *E. coli* Top 10 cells. Transformants were selected in LB agar ampicillin plates (Teknova). Plasmid DNA was prepared (Qiagen) and positive clones were sequenced to confirm insert sequence. One confirmed cloned plasmid for each was subsequently transformed into BL21 (DE3)(Invitrogen) for expression analysis.

I. DNA Sequencing

Sequencing reactions (Big dye version 3.1 (Applied Biosystems)) were purified using G-50 (Sigma) and loaded into the ABI3100 sequencer.

J. High Throughput (HTP) Expression Analysis

The *P. fluorescens* strains were analyzed using the standard Dow HTP expression protocol. Briefly, seed cultures grown in M9 medium supplemented with 1% glucose and trace elements were used to inoculate 0.5 mL of defined minimal salts medium with 5% glycerol as the carbon source in a 2.0 mL deep 96-well plate. Following an initial growth phase at 30° C., expression via the Ptac promoter was induced with 0.3 mM isopropyl-β-D-1-thiogalactopyranoside (IPTG). Cell density was measured by optical density at 600 nm ($OD_{600}$).

K. Preparation of HTP Samples for SDS-PAGE Analysis

Soluble and insoluble fractions from culture samples were generated using EASY LYSE™ (Epicentre Technologies cat#RP03750). The 25 μL whole broth sample was lysed by adding 175 mL of EASY LYSE™ buffer, incubating with gentle rocking at room temperature for 30 minutes. The lysate was centrifuged at 14,000 rpm for 20 minutes (4° C.) and the supernatant removed. The supernatant was saved as the soluble fraction. The pellet (insoluble fraction) was then resuspended in an equal volume of lysis buffer and resuspended by pipetting up and down. For selected clones, cell free broth samples were thawed and analyzed without dilution.

L. Expression and Analysis of Secretion of Proteins or Polypeptides of Interest

The seed cultures, grown in 1×M9 supplemented with 1% glucose (Teknova), supplemented with trace element solution were used to inoculate 50 mL of Dow defined minimal salts medium at 2% inoculum, and incubated at 30° C. with shaking. Cells were induced with 0.3 mM IPTG (isopropyl β-D-thiogalactopyranoside) ~24 hours elapsed fermentation time (EFT). Samples were taken at time of induction (I0) and 16 (I16), 24 (I24), or 40 (I40) hours post induction for analyses. Cell density was measured by optical density at 600 nm ($OD_{600}$). The cell density was adjusted to $OD_{600}$=20, and 1 mL was centrifuged at 14000×g for five minutes. Supernatants (cell free broth) were pipetted into a new microfuge tube, then cell pellets and cell free broth samples were frozen at −80° C. for later processing.

M. SDS-PAGE Analysis

Soluble and insoluble fractions from shake flask samples were generated using EASY LYSE™ Buffer (Epicentre Technologies). The frozen pellet was resuspended in 1 mL of lysis buffer. Fifty microliters were added to an additional 150 uL EASY LYSE™ buffer and incubated with shaking at room temperature for 30 minutes. The lysate was centrifuged at 14,000 rpm for 20 minutes (4° C.) and the supernatant removed. The supernatant was saved as the soluble fraction. The pellet was then resuspended in an equal volume (200 μL) of lysis buffer and resuspended by pipetting up and down; this was saved as the insoluble fraction. Cell free broth samples were thawed and used at full strength.

N. Western Analysis

Soluble and insoluble fractions prepared and separated by SDS-PAGE were transferred to nitrocellulose (BioRad) using 1× transfer buffer (Invitrogen) prepared according to manufacturer's protocol, for 1 hour at 100V. After transfer, the blot was blocked with POLY-HRP diluent (Research Diagnostics, Inc.) and probed with a 1:5,000 dilution of anti His tag antibody (Sigma or US Biologicals). The blot was washed with 1×PBS-Tween and subsequently developed using the Immunopure Metal Enhanced DAB Substrate Kit (Pierce).

O. 20 L Fermentation

The inocula for the fermentor cultures were each generated by inoculating a shake flask containing 600 mL of a chemically defined medium supplemented with yeast extract and glycerol with a frozen culture stock. After 16-24 hr incubation with shaking at 32° C., the shake flask culture was then aseptically transferred to a 20 L fermentor containing a medium designed to support a high biomass. Dissolved oxygen was maintained at a positive level in the liquid culture by regulating the sparged air flow and the agitation rates. The pH was controlled at the desired set-point through the addition of aqueous ammonia. The fed-batch high density fermentation process was divided into an initial growth phase of approximately 24 hr and gene expression phase in which IPTG was added to initiate recombinant gene expression. The expression phase of the fermentation was then allowed to proceed for 24 hours.

P. N-Terminal Amino Acid Sequence Analysis

Samples were run as described in SDS-PAGE analysis above and transferred to a Criterion Sequi-Blot PVDF membrane (Biorad). The membrane was stained with GelCode Blue stain reagent (Pierce) and subsequently destained with 50% methanol 1% acetic acid, rinsed with 10% methanol followed by de-ionized water, then dried. Bands of interest were sliced from the membrane, extracted and subjected to 8 cycles of Edman degradation on a Procise protein sequencing system, model 494 (Applied Biosystems, Foster City, Calif.). P. Edman, *Acta Chem. Scand.* 4, 283 (1950); review R. A. Laursen et al., *Methods Biochem. Anal.* 26, 201-284 (1980).

II. Results

A. Identification of Native Secretion Signal Sequences by Transposon Mutagenesis To identify *P. fluorescens* signal sequences that would secrete a heterologous protein to the periplasm or broth, a secretion reporter gene was cloned into a transposome. The secretion reporter gene used is an *E. coli* alkaline phosphatase gene (phoA) without a start codon or N-terminal signal sequence. PhoA is active in the periplasm (but not the cytosol) due to the formation of intramolecular disulfide bonds that allow dimerization into the active form (Derman et al. 1991). A similar method referred to as "genome scanning" was used to find secreted proteins in *E. coli* (Bailey et al 2002). The phoA gene has also been used to analyze secretion signals in periplasmic, membrane, and exported proteins in *E. coli* (Manoil et al. 1985) and in other bacteria (Gicquel et al. 1996). After electroporation and plating on indicator media, eight blue colonies were isolated. The insertion site of the transposome in the genome was sequenced and used to search a proprietary genome database of *P. fluorescens* MB101. Eight gene fusions identified as able to express active PhoA are shown in Table 6.

B. Cloning of Signal Sequence-Gal2 Fusions

The signal sequences of the secreted proteins identified above, outer membrane porin F (OP), phosphate binding protein porE (PB), iron binding protein (IB), azurin (AZ), lipoprotein B (L) and lysine-ornithine-arginine binding protein (LOA) were predicted using the SignalP program (J. D. Bendtsen 2004). Signal sequences for OP, PE and AZ have been previously identified in other systems [Arvidsson, 1989 #25; De, 1995 #24; Yamano, 1993 #23]. The activity of an additional secretion leader identified in another study, pbpA20V (Schneider et al. 2006), was also analyzed in parallel. In this study the coding region of six native *P. fluorescens* signal sequences, and a mutant of the *P. fluorescens* phosphate binding protein signal sequence (see Table 6) were each fused to the gal2 scFv gene using splicing by overlap extension PCR (SOE-PCR) as described in Materials and Methods such that the N-terminal 4 amino acids of Gal2 following cleavage of the signal peptide would be AQVQ. Repeated attempts to amplify the LAO signal sequence failed, and this signal sequence was dropped from further analysis. The gene fusions were cloned into the *P. fluorescens* expression vector pDOW1169 and transformed into DC454 host strain (ΔpyrF lsc::lacI$^{Q1}$). The resultant strains were subsequently assessed for Gal2 scFv expression and proper processing of the secretion leaders.

C. Expression of Secreted Gal2 scFv

At the shake flask scale, fusions of PB, OP, PO, AZ, IB, and L to gal2 scFv achieved the expected OD$_{600}$, except for L-gal2 scFv, which failed to grow following subculture into production medium (data not shown). Western blot analysis confirmed that the PB, OP, PO, AZ and IB signal sequences were cleaved from the Gal2 scFv fusion. However Western analysis showed the presence of unprocessed PB-Gal2 and OP-Gal2. Some soluble Gal2 scFv expressed from AZ and IB fusions was found in the cell-free-broth, indicating that soluble protein was expressed and leaked from the periplasmic space. Amino terminal sequence analysis was performed to confirm the cleavage of the signal sequence. Insoluble Gal2 protein expressed from the azurin (pDOW1191) fusions shows a mixture of protein with processed and unprocessed secretion signal. However, the signal sequence was observed to be fully processed from the IB-Gal2 fusion.

Expression of Gal2 scFv fused to each of seven leaders was evaluated at the 20 L fermentation scale using standard fermentation conditions. All strains grew as expected, reaching induction OD$_{600}$ (~180 units) at 18-24 hours. The lipB-Gal2 strain grew slightly more slowly than other strains. This was not wholly unexpected as the lipB-Gal2 strain did not grow following inoculation of shake flask medium at small scale fermentation. Expression and processing of the Gal2 scFv was assessed by SDS-PAGE and Western blot. SDS-PAGE analysis showed that high levels of Gal2 was expressed when fused to either the OP or PB secretion signals. However, only a portion (~50%) of the OP-Gal2 fusion protein appeared to be secreted to the periplasm with the signal sequence cleaved. As observed at small scale, Gal2 was expressed predominantly in the insoluble fraction, although soluble protein was detected by Western blot. A small amount of protein was also detected in the culture supernatant, indicating leakage from the periplasm (FIG. 7). N-terminal sequence analysis confirmed that the ibp and azurin leaders were processed as expected, resulting in the N-terminal amino acid sequence AQVQL (SEQ ID NO:44). Likewise, the PorE secretion leader appeared to be processed by Western analysis and was confirmed by N-terminal analysis. The level of insoluble PorE-Gal2 expression was slightly lower than that of insoluble ibp-Gal2 and azurin-Gal2. LipB-Gal2 showed expression of processed Gal2 at levels similar to that of PorE-Gal2. The greatest amount of protein was observed from strains expressing pbp-Gal2 and pbpA20V-Gal2. The amount of Gal2 expressed from the pbpA20V-Gal2 strain appeared to be even higher than that produced by the pbp-Gal2 strains (FIG. 6). Soluble processed Gal2 was detected by Western analysis, as was a mixture of unprocessed and processed insoluble protein (FIG. 7). N-terminal sequence analysis of the insoluble protein confirmed a mixture of unprocessed and correctly processed Gal2.

Example 3

Identification of Bce Leader Sequence

I. Materials and Methods

BceL is a secretion leader that was identified to be encoded by part of DNA insert containing a gene for a hydrolase from *Bacillus coagulans* CMC 104017. This strain *Bacillus coagulans* is also known as NCIMB 8041, ATCC 10545 and DSMZ 2311 in various commercial culture collections, and has it's origins as NRS784. NRS 784 is from the NR Smith collection of Spore forming bacteria (Smith et al Aerobic spore forming bacteria US. Dep. Agr. Monogra. 16:1-148 (1952)). The other original reference for this strain cited by NCIMB is Cambell, L. L. and Sniff E. E. (1959. J. Bacteriol. 78:267 An investigation of Folic acid requirements of *Bacillus coagulans*).

Sequence and Bioinformatics Analysis

A DNA insert of 4,127 bp from *Bacillus coagulans* CMC 104017 was sequenced and analyzed to localize coding sequences potentially encoding a hydrolase enzyme. One coding sequence of 1,314 bp, designated CDS1, was identified behind the lac promoter at the 5' end. The DNA and predicted protein sequences for CDS1 are set forth in SEQ ID NO:45 and 46, respectively. CDS1 was determined most likely to encode a hydrolase based upon BLASTP analysis of the predicted protein sequence. The CDS1 sequence showed homology (E-value: $2e^{-36}$) to beta-lactamase from Rhodopseudomonas palustris HaA2. SignalP 3.0 hidden Markov model analysis (Bendtsen J D, Nielson G, von Heijne G, Brunak S: Improved prediction of signal peptides: Signal 3.0. *J. Mol. Biol.* 2004, 340:783.) of CDS1 predicted the presence of a signal sequence for the organism class Gram-positive bacteria with a signal peptidase cleavage site between residues 33/34 of SEQ ID NO:46.

Construction of Protein Expression Plasmids

Standard cloning methods were used in the construction of expression plasmids (Sambrook J, Russell D: Molecular Cloning a Laboratory Manual, third edn. Cold Spring Harbor: Cold Spring Harbor Press; 2001). DNA sequence fusions were performed using the SOE-PCR method (Horton, R. M., Z. Cai, S, N. Ho and L. R. Pease (1990). "Gene splicing by overlap extension: tailor-made genes using the polymerase chain reaction." BioTechniques 8(5): 528-30, 532, 534-5)). Phusion DNA polymerase (New England Biolabs cat#F531S) was used for all PCR reactions.

Plasmids were designed to express and localize an esterase protein from *Bacillus coagulans* CMC 104017 into either the cytoplasm or periplasmic space of *P. fluorescens*. The final PCR products were digested with the SpeI and XhoI restriction endonucleases (New England Biolabs cat.#R0133 and #R0146) then ligated into expression vector pDOW1169, also digested with SpeI and XhoI, using T4 DNA ligase (New England Biolabs cat.#M0202S) to produce the cytoplasmic CMC104641 CDS-1 expression vector p484-001 and the native Bce leader CMC 104641 CDS-1 expression vector p484-002. The ligation reaction mixtures were then transformed into *P. fluorescens* strain DC454 (ΔpyrF, lacI$^{Q1}$) by electroporation, recovered in SOC-with-soy medium (Teknova cat#2S2699) and plated on selective medium (M9 glucose agar, Teknova cat#2M1200). Colonies were analyzed by restriction digestion of miniprep plasmid DNA (Qiagen, cat.#27106). Ten clones from each transformation were sequenced to confirm correct insert.

Expression Analysis

The *P. fluorescens* strain DC454 carrying each clone was examined in shake-flasks containing 200 mL of defined minimal salts medium with 5% glycerol as the carbon source ("Dow Medium"). Following an initial growth phase, expression via the tac promoter was induced with 0.3 mM isopropyl-β-D-1-thiogalactopyranoside (IPTG). Cultures were sampled at the time of induction (I0), and at 24 hours post induction (I24). Cell density was measured by optical density at 600 nm ($OD_{600}$). A table showing the shake flask numbering scheme is shown in Table 7.

TABLE 7

| Host Strain | Plasmid number (leader-gene) | Flask Number | | |
|---|---|---|---|---|
| DC454 | P484-001 (cytoplasmic 484) | EP484-001 | EP484-002 | EP484-003 |
| DC454 | P484-002 (native leader 484) | EP484-004 | EP484-005 | EP484-006 |

At each sampling time, the cell density of samples was adjusted to $OD_{600}$=20 and 1 mL aliquots were centrifuged at 14000×g for five minutes. Supernatants (cell free broth) were pipetted into a new microfuge tube then cell pellets and cell free broth samples were frozen at −20° C.

Cell Lysis and SDS-PAGE Analysis

Soluble and insoluble fractions from shake flask samples were generated using Easy Lyse (Epicentre Technologies). The frozen pellet was resuspended and diluted 1:4 in lysis buffer and incubated with shaking at room temperature for 30 minutes. The lysate was centrifuged at 14,000 rpm for 20 minutes (4° C.) and the supernatant removed. The supernatant was saved as the soluble fraction. The pellet (insoluble fraction) was then resuspended in an equal volume of lysis buffer and resuspended by pipetting up and down. Cell free broth samples were thawed and used at full strength. Samples were mixed 1:1 with 2× Laemmli sample buffer containing β-mercaptoethanol (BioRad cat# 161-0737) and boiled for 5 minutes prior to loading 20 L on a Bio-Rad Criterion 10% Criterion XT gel (BioRad cat# 45-0112) and separated by electrophoresis in the recommended 1×MOPS buffer (cat.# 161-0788 Lot# 210001188). Gels were stained with SIMPLYBLUE™ SafeStain (Invitrogen cat# LC6060) according to the manufacturer's protocol and imaged using the Alpha Innotech Imaging system. The protein quantity of gel bands of interest were estimated by comparison to BSA protein standards loaded to the same gel.

II. Results

Figure 8:
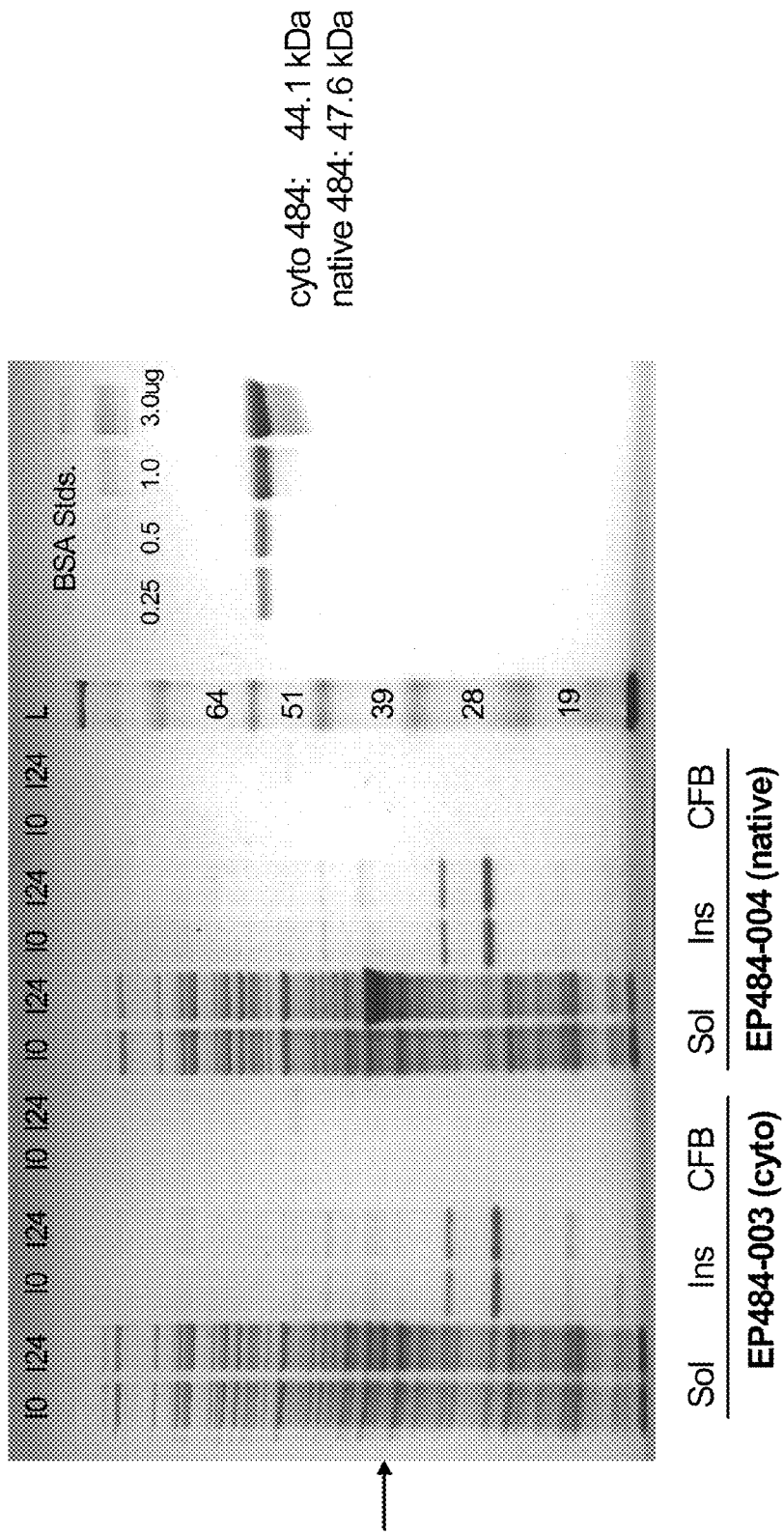
FIG. 8 shows an SDS-PAGE analysis of EP484-003 and EP484-004 fractions. Representative results of SDS-PAGE analyses are shown. Molecular weight markers (L) are shown at the center. BSA standards (BSA Stds.) are indicated. The arrow indicates induced band. Below each lane is the fraction type: soluble (Sol), insoluble (Ins), or cell-free broth (CFB). Above each lane is the sample time at induction (I0), or 24 hours post induction (I24). The strain number is shown below each grouping of samples. The large protein band in the I24 soluble fraction of EP484-004 corresponds to enhanced gene expression facilitated by Bce leader sequence.

A total of six shake flasks (3 flasks per strain) were used to evaluate hydrolase expression. Growth of the periplasmic and cytoplasmic designed strains were consistent with normal growth for *P. fluorescens* strains, reaching an $OD_{600}$ of approximately 15 at twenty-four hours post induction. SDS-PAGE analysis was performed to assess hydrolase (CDS1 protein) expression at the time of induction and 24 hours post-induction. Soluble, insoluble, and cell free broth fractions were analyzed by SDS-PAGE. For the cytoplasmic CDS-1 strain (p484-001), protein of the expected size for cytoplasmic hydrolase (44.1 kDa) accumulated almost entirely in the soluble fraction at 124 (24 hours following IPTG induction) in all three isolates at an estimated yield of 0.1 mg/mL. FIG. 8 shows representative results for the cytoplasmic strain evaluated as EP484-003. A negligible band of expected size was detectable in the insoluble fraction and no CDS1 protein was detected in the cell-free broth. For the periplasmic strain expressing the native Bce leader-CDS1 (p484-002), protein of the expected size for native esterase accumulated almost entirely in the soluble fraction at 124 in all three isolates at an estimated yield of 0.8 mg/mL. FIG. 8 shows representative results for the periplasmic strain containing the Bce leader fusion evaluated as EP484-004. It was unclear if the expressed native esterase was entirely processed since the gel loading used made it difficult to discern between the predicted unprocessed size of 47.6 kDa and processed size of 44.1 kDa. Similar to results with the cytoplasmic expression strain, a negligible band of expected size was detectable in the insoluble fraction and no CDS1 protein was detected in the cell-free broth. The translated sequence of the Bce Leader of interest is set forth in SEQ ID NO:8.

Example 4

Identification and Analysis of *P. fluorescens* Secretion Leaders 6,433 translated ORFs from the MB214 genome were analyzed with the signal peptide prediction program, SignalP 2.0 (Nielsen, H., et al. Protein Eng, 1997. 10(1): p. 1-6). 1326 were predicted by the HMM model to contain a signal peptide. These proteins were analyzed with PsortB 2.0 (Gardy, J. L., et al. Bioinformatics, 2005. 21(5): p. 617-23) and all those with a PsortB final localization identified as cytoplasmic or cytoplasmic membrane were removed leaving 891. 82 proteins for which the SignalP HMM probability of containing a signal peptide was below 0.79 were removed yielding 809. The cutoff of 0.79 was chosen because that was the highest value that did not exclude aprA (RXF04304, known to be an extracellular protein). The amino terminal sequences of these 809 translated ORFs containing the signal peptide as predicted by the SignalP Neural Network algorithm plus the first 7 amino acids of the processed protein were aligned using CLUSTALX 1.81 (Thompson, J. D., et al. Nucleic Acids Res, 1997. 25(24): p. 4876-82).

Huber et al. suggest that highly hydrophobic signal sequences are more likely to be co-translationally secreted (Huber, D., et al. J Bacteriol, 2005. 187(9): p. 2983-91). For the purpose of identifying co-translationally secreted proteins the amino acid indexes of Wertz-Scheraga (WS)(Wertz, D. H. and H. A. Scheraga, Macromolecules, 1978. 11(1): p. 9-15), were found to be the best. For this study, these indexes were obtained from AAindex on the worldwide web at www-.genomejp/dbget-bin/www_bget?aax1:WERD780101. An algorithm reported by Boyd (Boyd, D., C. Schierle, and J. Beckwith, Protein Sci, 1998. 7(1): p. 201-5), was modified and used to rank the 809 proteins based on hydrophobicity. The algorithm scans each sequence averaging the WS scores within a window of 12. The most hydrophobic region is used to assign the WS score for the whole protein. This yielded 142 signal sequences with WS scores greater than 0.69, the cutoff defined in Huber et. al. This smaller list was cross-referenced with data from 2D-LC whole proteome experiments performed by the Indiana Centers for Applied Protein Sciences (INCAPS). These experiments attempted to identify and quantify all proteins expressed in MB214 (descended from *P. fluorescens* MB101) under a variety of growth conditions. A protein that appears in this list with high maximum expression levels is likely to be highly expressed. In these data a priority score of 1 or 3 indicates high confidence in the identification of the protein. The proteins from the list of 142 which were identified in the INCAPS experiments with a priority of 1 or 3 are listed in Table 8 in order of their maximum expression levels.

TABLE 8

7 unique proteins from the list of 142 with priority 1 or 3 (indicating high confidence in the identification) listed in order of maximum expression levels found during the INCAPS experiments.

| Priority | Protein ID | Curated Function | Max |
|---|---|---|---|
| 1 | RXF05550.1 | tetratricopeptide repeat family protein | 377264.2 |
| 1 | RXF08124.1 | Methyl-accepting chemotaxis protein | 134887.4 |
| 1 | RXF07256.1 | TolB protein | 88429.16 |
| 3 | RXF07256.1_a1 | TolB protein | 84020.51 |
| 3 | RXF04046.2_a1 | cytochrome c oxidase, monoheme subunit, membrane-bound (ec 1.9.3.1) | 79275.3 |
| 3 | RXF03895.1_a1 | asma | 50164.08 |
| 3 | RXF07256.1_pn | TolB protein | 49215.09 |
| 1 | RXF06792.1 | Conserved Hypothetical Protein | 47485.35 |
| 3 | RXF02291.1 | toluene tolerance protein ttg2C | 45703.08 |

Several co-translationally secreted proteins in *E. coli* have been identified. The sequences of several of these were used to search the MB214 genome for homologues. The *E. coli* genes were: DsbA, TorT, SfmC, FocC, CcmH, YraI, TolB, NikA, FlgI. The BLASTP algorithm (Altschul, S. F., et al., J Mol Biol, 1990. 215(3): p. 403-10) was used to search a database of MB214 translated ORFs. The MB214 proteins were placed into two categories based on the degree of homology they showed to their *E. coli* counterparts. High homology proteins matched with expect scores of $2e^{-84}$ or better. Low homology proteins had expect scores between $8e^{-17}$ and $5e^{-32}$. This method yielded 111 unique potential homologues, some of which overlapped with the 7 targets obtained above.

The combined list of 18 unique proteins were analyzed using SignalP and 9 final targets which were predicted to have a single likely signal peptidase cut site were chosen for expression studies.

Isolation and Sequence Analysis of Secretion Leaders

The identified *P. fluorescens* secretion leaders were amplified from DC454 (descended from *P. fluorescens* MB 101) genomic DNA and cloned into pCRBLUNTII-TOPO (Invitrogen) for DNA sequence verification. The DNA and deduced amino acid sequence of each *P. fluorescens* secretion leader isolated is referenced in Table 9.

TABLE 9

*P. fluorescens* secretion leader sequences

| LEADER | DNA SEQ ID NO: | AMINO ACID SEQ ID NO: |
|---|---|---|
| CupA2 | 9 | 10 |
| CupB2 | 11 | 12 |
| CupC2 | 13 | 14 |
| TolB | 49 | 50 |
| NikA | 15 | 16 |
| FlgI | 17 | 18 |
| ORF5550 | 19 | 20 |
| Ttg2C | 21 | 22 |
| ORF8124 | 23 | 24 |

Figure 9:
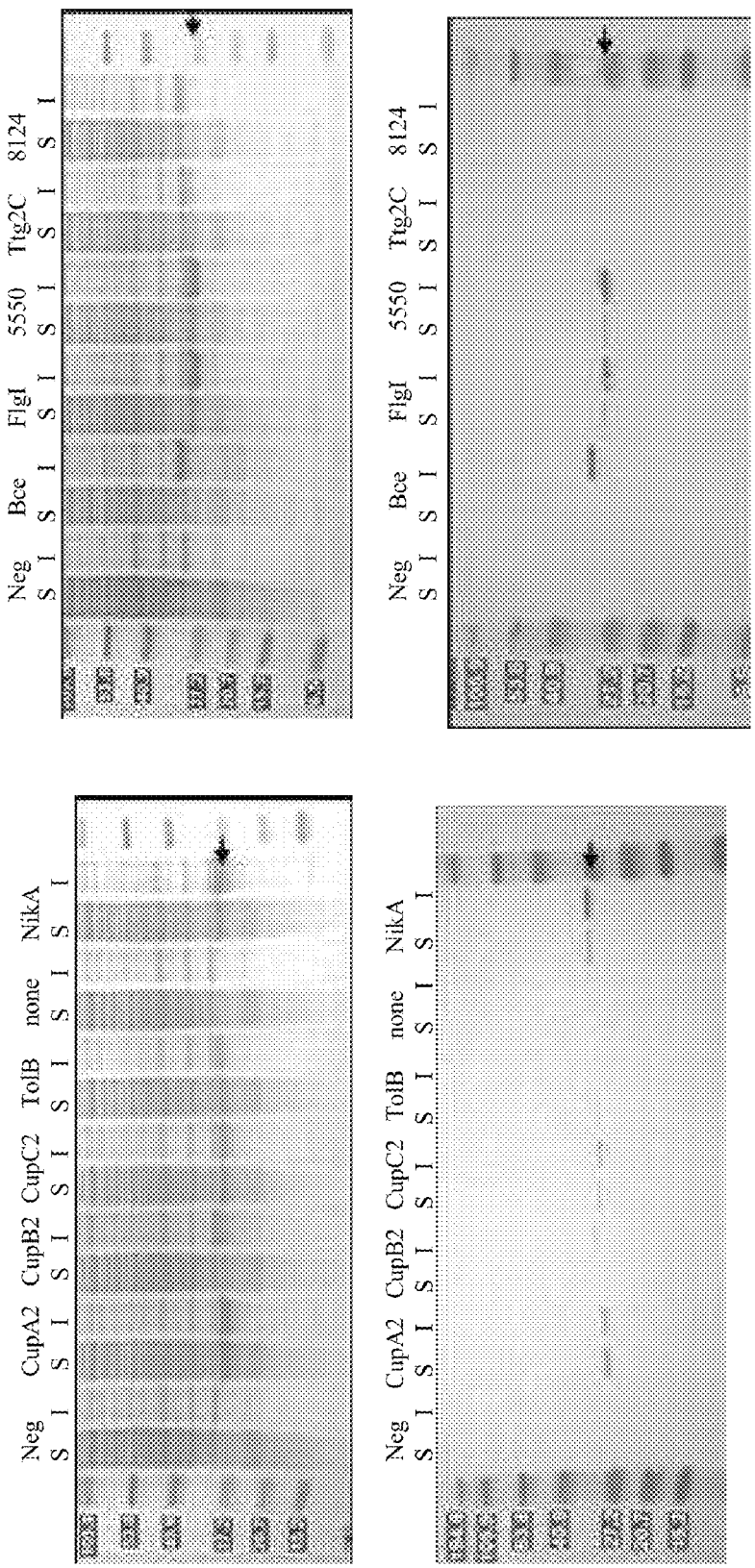
FIG. 9 demonstrates SDS-PAGE and Western analyses of Gal2 scFv expression. Soluble (S) and Insoluble (I) fractions were analyzed. Above each pair of lanes is indicated the secretion leader fused to Gal2. Molecular weight markers are described to the left of each SDS-PAGE gel (top) or Western blot (bottom). Arrows indicate the migration of Gal2.

Fusion of Secretion Leaders to Gal2 scFv and *E. Coli* Thioredoxin and Expression Analysis Each secretion leader (Table 9) was fused in frame to the Gal2 scFv sequence (Martineau, P. et al. 1998 J. Mol. Bio. 280:117) and/or the *E. coli* thioredoxin (TrxA) sequence (SEQ ID NO:46) using splicing by overlap extension PCR (Horton R. M. et al. 1990 Biotechniques 8:528). The resulting fragments were purified and subsequently used as template for a second round of PCR to fuse NikA secretion leader coding sequence to the trxA sequence. The fusions were then cloned into the *P. fluorescens* expression vector pDOW1169 under control of the tac promoter. Each construct was transformed into *P. fluorescens* DC454 and expression was assessed in high throughput format. Cultures were grown in a defined mineral salts medium supplemented with 5% glycerol in 2 mL deep well plates at a culture volume of 0.5 mL. Following a 24 hour growth period, the recombinant protein was induced with 0.3 mM IPTG and allowed to express for 24 hours. Cultures were fractionated by sonication and protein expression and secretion leader processing was assessed by SDS-CGE and Western blot (FIG. 9). Each of the leaders tested, with the exception of the Bce leader, was found to be partially or fully processed from the Gal2 scFv protein sequence. Each also greatly improved expression of Gal2 scFv compared to an expression strain that encodes cytoplasmic Gal2 scFv (none), indicating that in addition to directing the subcellular localization, these secretion leaders can also improve overall expression. Not unexpectedly, varying levels of expression and solubility of Gal2 scFv were also observed. Western analysis confirmed that some soluble Gal2 was produced when fused to the CupA2, CupC2, NikA, FlgI and ORF 5550 (FIG. 9). Although expression of TolB leader fused to Gal2 was lower than observed with the other leaders, Western analysis showed that all protein expressed was soluble. N-terminal analysis showed that the TolB, CupA2, CupC2, FlgI, NikA and ORF5550 leaders were cleaved from Gal2 scFv as expected (data not shown).

Figure 10:
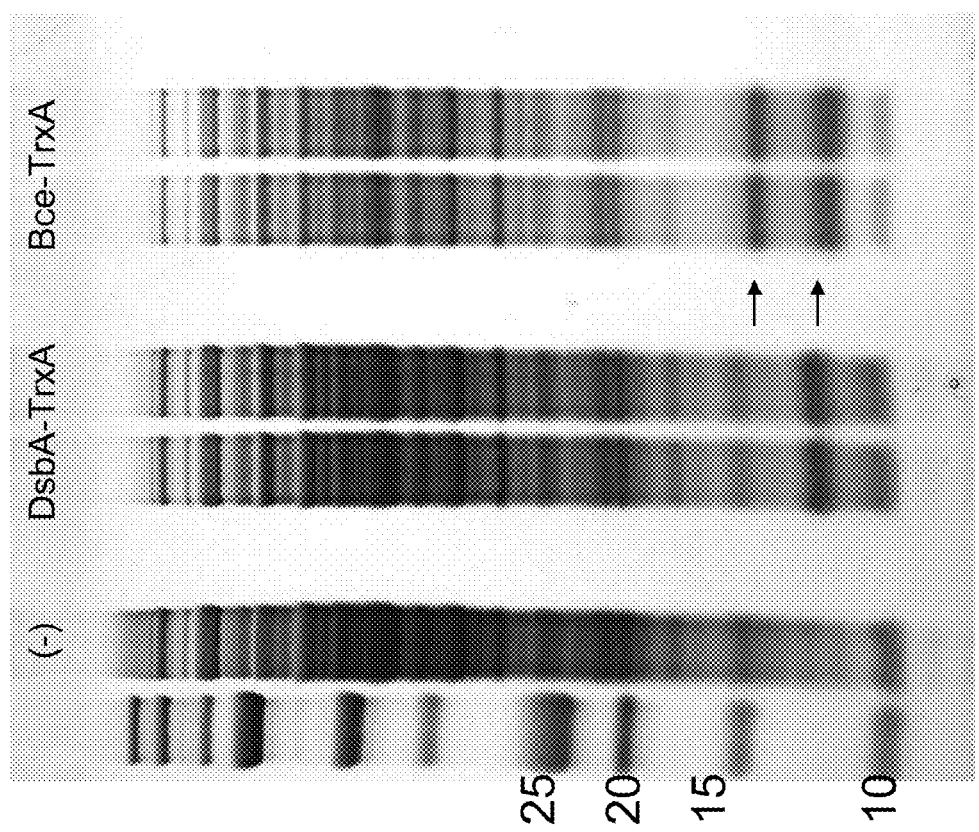
FIG. 10 represents an SDS-PAGE Analysis of Thioredoxin (TrxA) expression. Soluble fractions were analyzed. Above each pair of lanes is indicated the secretion leader fused to TrxA. Molecular weight markers are described to the left of the SDS-PAGE gel. Arrows indicate the migration of unprocessed (upper arrow) and processed (lower arrow) TrxA.

Although not processed from Gal2 scFv, the Bce leader was found to be processed from TrxA (FIG. 10). Thioredoxin has been described as a model protein for identification of co-translational secretion leaders as it folds rapidly in the cytoplasm (Huber et al. 2005 J. Bateriol. 187:2983). The successful secretion of soluble TrxA utilizing the Bce leader may indicate that this leader acts in a co-translational manner to facilitate periplasmic secretion.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a secretion signal coding sequence for a secretion polypeptide selected from the group consisting of:
   a) a nucleic acid molecule comprising the nucleotide sequence of SEQ ID NO:3; and
   b) a nucleic acid molecule which encodes a polypolypeptide comprising the amino acid sequence of SEQ ID NO:4.

2. The nucleic acid molecule of claim 1, wherein said nucleic acid molecule has been adjusted to reflect the codon preference of a host organism selected to express the nucleic acid molecule.

3. A vector comprising a secretion signal coding sequence selected from the group consisting of:
   a) a nucleic acid molecule comprising the nucleotide sequence of SEQ ID NO:3; and
   b) a nucleic acid molecule which encodes a polypolypeptide comprising the amino acid sequence of SEQ ID NO:4.

4. The vector of claim 3, wherein said nucleic acid molecule has been adjusted to reflect the codon preference of a host organism selected to express the nucleic acid molecule.

5. The vector of claim 3, wherein the secretion signal coding sequence is operably linked to a sequence encoding a protein or polypeptide of interest.

6. The vector of claim 5, wherein the protein or polypeptide of interest is native to a host organism in which the protein or polypeptide of interest is expressed.

7. The vector of claim 3, wherein the protein or polypeptide of interest is native to P. fluorescens.

8. The vector of claim 5, wherein the protein or polypeptide of interest is obtained from a protein or polypeptide that is not native to a host organism in which the protein or polypeptide of interest is expressed.

9. The vector of claim 5, wherein the protein or polypeptide of interest is from an organism that is not a Pseudomonad.

10. The vector of claim 3, wherein the protein or polypeptide of interest is obtained from a eukaryotic organism.

11. The vector of claim 10, wherein the protein or polypeptide of interest is obtained from a mammalian organism.

12. The vector of claim 5, further comprising a sequence encoding a linkage sequence between the signal coding sequence and a sequence encoding the protein or polypeptide of interest.

13. The vector of claim 12, wherein the linkage sequence is cleavable by a signal peptidase.

14. The vector of claim 5, wherein the sequence encoding the protein or polypeptide sequence of interest is operably linked to a sequence encoding a second signal sequence.

15. The vector of claim 14, wherein the second signal sequence comprises a sequence targeted to an outer membrane secretion signal.

16. The vector of claim 3, wherein the vector further comprises a promoter.

17. The vector of claim 16, wherein the promoter is native to a bacterial host cell.

18. The vector of claim 16, wherein the promoter is not native to a bacterial host cell.

19. The vector of claim 17, wherein the promoter is native to E. coli.

20. The vector of claim 16, wherein the promoter is an inducible promoter.

21. The vector of claim 16, wherein the promoter is a lac promoter or a derivative of a lac promoter.

22. A recombinant cell comprising a secretion signal coding sequence for a secretion polypeptide selected from the group consisting of:
   a) a nucleic acid molecule comprising the nucleotide sequence of SEQ ID NO:3; and b) a nucleic acid molecule which encodes a polypolypeptide comprising the amino acid sequence of SEQ ID NO:4.

23. The cell of claim 22, wherein the secretion signal coding sequence is in an expression vector.

24. The cell of claim 22, wherein the secretion signal coding sequence is operably linked to a sequence encoding a protein or polypeptide of interest.

25. The cell of claim 24, wherein the cell expresses the protein or polypeptide of interest operably linked to the secretion signal polypeptide.

26. The cell of claim 25, wherein the protein or polypeptide is expressed in a periplasmic compartment of the cell.

27. The cell of claim 25, wherein an enzyme in the cell cleaves the secretion signal polypeptide from the protein or polypeptide of interest.

28. The cell of claim 22, wherein the cell is obtained from a bacterial host.

29. The cell of claim 28, wherein the host is a Pseudomonad.

30. The cell of claim 29, wherein the host is a P. fluorescens.

31. The cell of claim 28, wherein the host is an E. coli.

32. An expression system for expression of a protein or polypeptide of interest comprising:
  a) a host cell; and,
  b) a vector comprising a nucleic acid molecule encoding the protein or polypeptide of interest operably linked to a secretion signal polypeptide selected from the group consisting of:
    i) a nucleic acid molecule comprising the nucleotide sequence of SEQ ID NO:3; and
    ii) a nucleic acid molecule which encodes a polypolypeptide comprising the amino acid sequence of SEQ ID NO:4.

33. The expression system of claim 32, wherein the host cell expresses the protein or polypeptide of interest operably linked to the secretion signal polypeptide.

34. The expression system of claim 33, wherein the protein or polypeptide of interest is expressed in a periplasmic compartment of the cell.

35. The expression system of claim 33, wherein an enzyme in the cell cleaves the signal polypeptide from the protein or polypeptide of interest.

36. The expression system of claim 32, wherein the cell is obtained from a bacterial host.

37. The expression system of claim 32, wherein the host is a Pseudomonad.

38. The expression system of claim 37, wherein the host is P. fluorescens.

39. The expression system of claim 36, wherein the host is E. coli.

40. The expression system of claim 32, further comprising a fermentation medium.

41. The expression system of claim 40, wherein the fermentation medium comprises a chemical inducer.

42. A method for the expression of a recombinant protein in a host cell comprising providing a host cell comprising a vector encoding a protein or polypeptide of interest operably linked to a secretion signal polypeptide selected from the group consisting of:
  i) a nucleic acid molecule comprising the nucleotide sequence of SEQ ID NO:3; and
  ii) a nucleic acid molecule which encodes a polypolypeptide comprising the amino acid sequence of SEQ ID NO:4.

43. The method of claim 42, wherein the cell is grown in a mineral salts media.

44. The method of claim 42, wherein the cell is grown at a high cell density.

45. The method of claim 44, wherein the cell is grown at a cell density of at least 20 g/L.

46. The method of claim 42, further comprising purifying the recombinant protein.

47. The method of claim 46, wherein the recombinant protein is purified by affinity chromatography.

48. The method of claim 42, wherein the operable linkage of the protein or polypeptide of interest and the secretion signal polypeptide is cleavable by an enzyme native to the host cell.

49. The method of claim 48, wherein the secretion signal polypeptide is cleaved from the protein or polypeptide of interest during expression.

50. The method of any claim 42, wherein the protein or polypeptide of interest is native to the organism from which the host cell is obtained.

51. The method of claim 42, wherein the protein or polypeptide of interest is native to a P. fluorescens organism.

52. The method of claim 42, wherein the protein or polypeptide of interest is not native to the organism from which the host cell is obtained.

53. The method of claim 42, wherein the protein or polypeptide of interest is obtained from an organism that is not a Pseudomonad.

54. The method of claim 42, wherein the protein or polypeptide of interest is obtained from a eukaryotic organism.

55. The method of claim 42, wherein the recombinant protein comprises a sequence that includes at least two cysteine residues.

56. The method of claim 42, wherein at least one disulfide bond is formed in the recombinant protein in the cell.

57. The method of claim 42, further comprising a linkage sequence between the signal polypeptide sequence and the sequence of the protein or polypeptide of interest.

58. The method of claim 50, wherein at least 50% of the protein or polypeptide of interest comprises a native amino terminus.

59. The method of claim 58, wherein at least 80% of the protein or polypeptide of interest comprises a native amino terminus.

60. The method of claim 59, wherein at least 90% of the protein or polypeptide of interest comprises a native amino terminus.

61. The method of claim 42, wherein at least 50% of the recombinant protein is active.

62. The method of claim 61, wherein at least 80% of the recombinant protein is active.

63. The method of claim 42, wherein at least 50% of the recombinant protein is expressed in a periplasmic compartment.

64. The method of claim 6, wherein at least 75% of the recombinant protein is expressed in a periplasmic compartment.

65. The method of claim 64, wherein at least 90% of the recombinant protein is expressed in a periplasmic compartment.

66. The method of claim 42, wherein the host cell is a Pseudomonad cell.

67. The method of claim 66, wherein the cell is a P. fluorescens cell.

68. The method of claim 42, wherein the cell is an E. coli cell.

* * * * *

UNITED STATES PATENT AND TRADEMARK OFFICE
CERTIFICATE OF CORRECTION

PATENT NO. : 7,618,799 B2  
APPLICATION NO. : 12/022789  
DATED : November 17, 2009  
INVENTOR(S) : Coleman et al.

Page 1 of 1

It is certified that error appears in the above-identified patent and that said Letters Patent is hereby corrected as shown below:

Title Page, Item (75) Inventor is corrected to read:
-- Russell J. Coleman, San Diego (CA);
Diane Retallack, Poway (CA);
Thomas M. Ramseier, Newton (MA);
Charles D. Hershberger, Poway (CA);
Stacey Lee, San Diego (CA) --.

Signed and Sealed this
Eighteenth Day of August, 2015

Michelle K. Lee
*Director of the United States Patent and Trademark Office*